United States Patent
Kim et al.

(10) Patent No.: US 7,580,740 B2
(45) Date of Patent: Aug. 25, 2009

(54) ATRIAL TACHYARRHYTHMIA DETECTION USING SELECTED ATRIAL INTERVALS

(75) Inventors: Jaeho Kim, Redmond, WA (US); Joseph M. Bocek, Seattle, WA (US); Anthony S. Harrington, Woodinville, WA (US); Harley G. White, Carnation, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 299 days.

(21) Appl. No.: 11/126,594

(22) Filed: May 11, 2005

(65) Prior Publication Data
US 2006/0259089 A1    Nov. 16, 2006

(51) Int. Cl.
*A61N 1/37* (2006.01)
*A61N 1/362* (2006.01)

(52) U.S. Cl. ............... 600/515; 600/509; 600/516; 600/518; 607/14

(58) Field of Classification Search ........... 600/509, 600/515, 516, 518

See application file for complete search history.

(56) References Cited

U.S. PATENT DOCUMENTS

| | | | | |
|---|---|---|---|---|
| 5,205,283 A | * | 4/1993 | Olson | 607/4 |
| 5,601,613 A | | 2/1997 | Florio et al. | |
| 5,658,320 A | * | 8/1997 | Betzold et al. | 607/14 |
| 5,683,428 A | * | 11/1997 | Franberg et al. | 607/14 |
| 5,759,196 A | * | 6/1998 | Hess et al. | 607/14 |
| 5,788,717 A | | 8/1998 | Mann et al. | |
| 5,792,192 A | | 8/1998 | Lu | |
| 5,814,083 A | | 9/1998 | Hess et al. | |
| 2002/0082660 A1 | * | 6/2002 | Stahmann et al. | 607/14 |

* cited by examiner

*Primary Examiner*—Carl H Layno
*Assistant Examiner*—Yun Haeng Lee
(74) *Attorney, Agent, or Firm*—Hollingsworth & Funk, LLC

(57) ABSTRACT

Methods and systems are directed to detecting atrial tachyarrhythmia. A plurality of A-A intervals is detected. The detected A-A intervals are selected and used to detect atrial tachyarrhythmia. Selecting A-A intervals may be based on determining that A-A intervals are qualified. Qualified A-A intervals may be determined if a duration of the particular A-A interval falls outside a predetermined duration range, for example. Qualified A-A intervals may also be determined based on events occurring between consecutively sensed atrial events of the particular A-A interval, and whether the duration of the particular A-A interval falls within the predetermined duration range, for example.

6 Claims, 18 Drawing Sheets

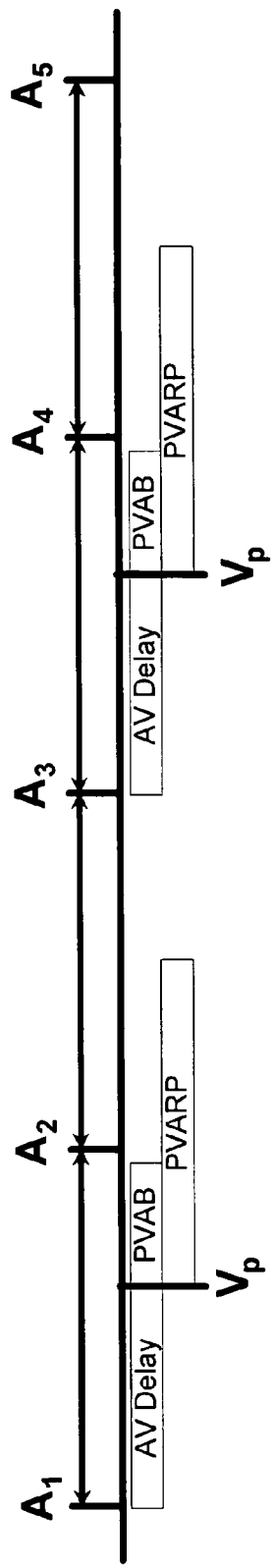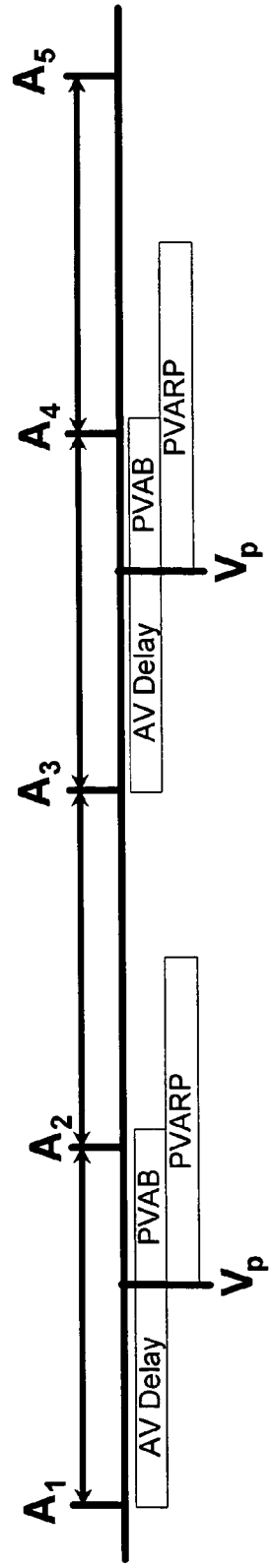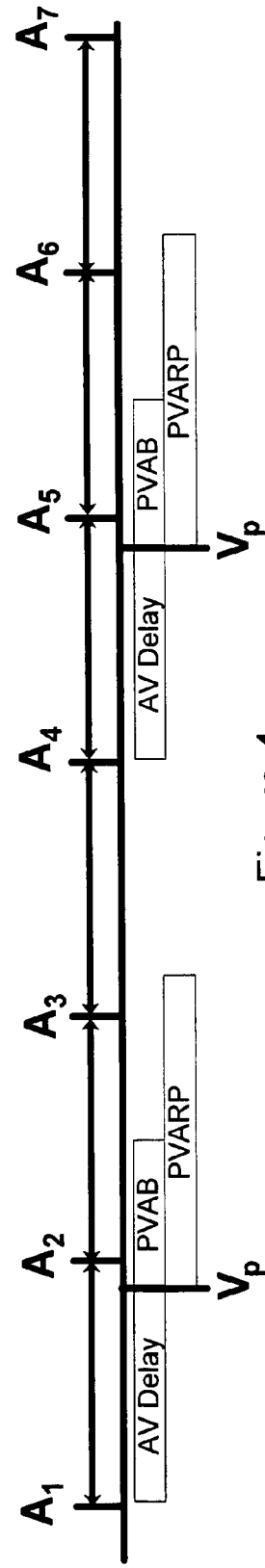
Figure 2
Figure 3
Figure 4

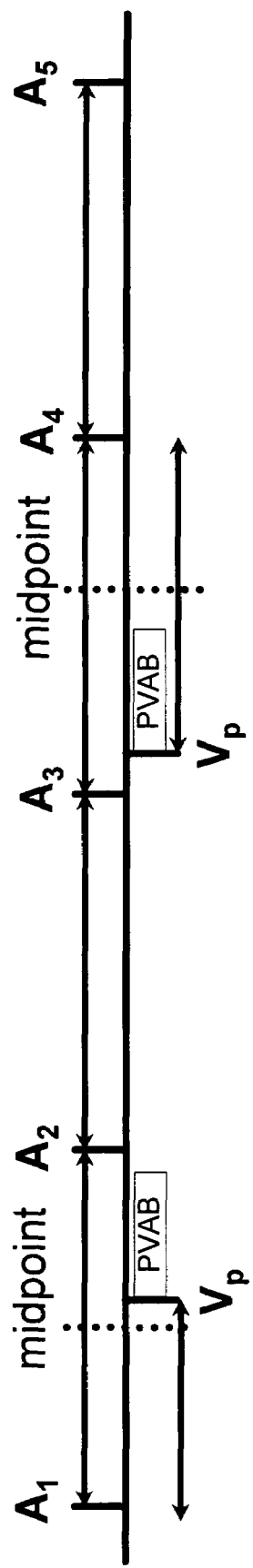
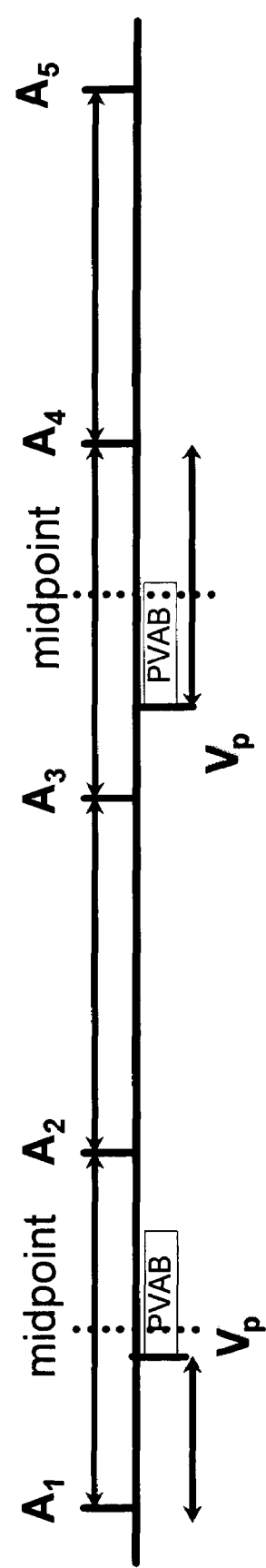
Figure 6A
Figure 6B

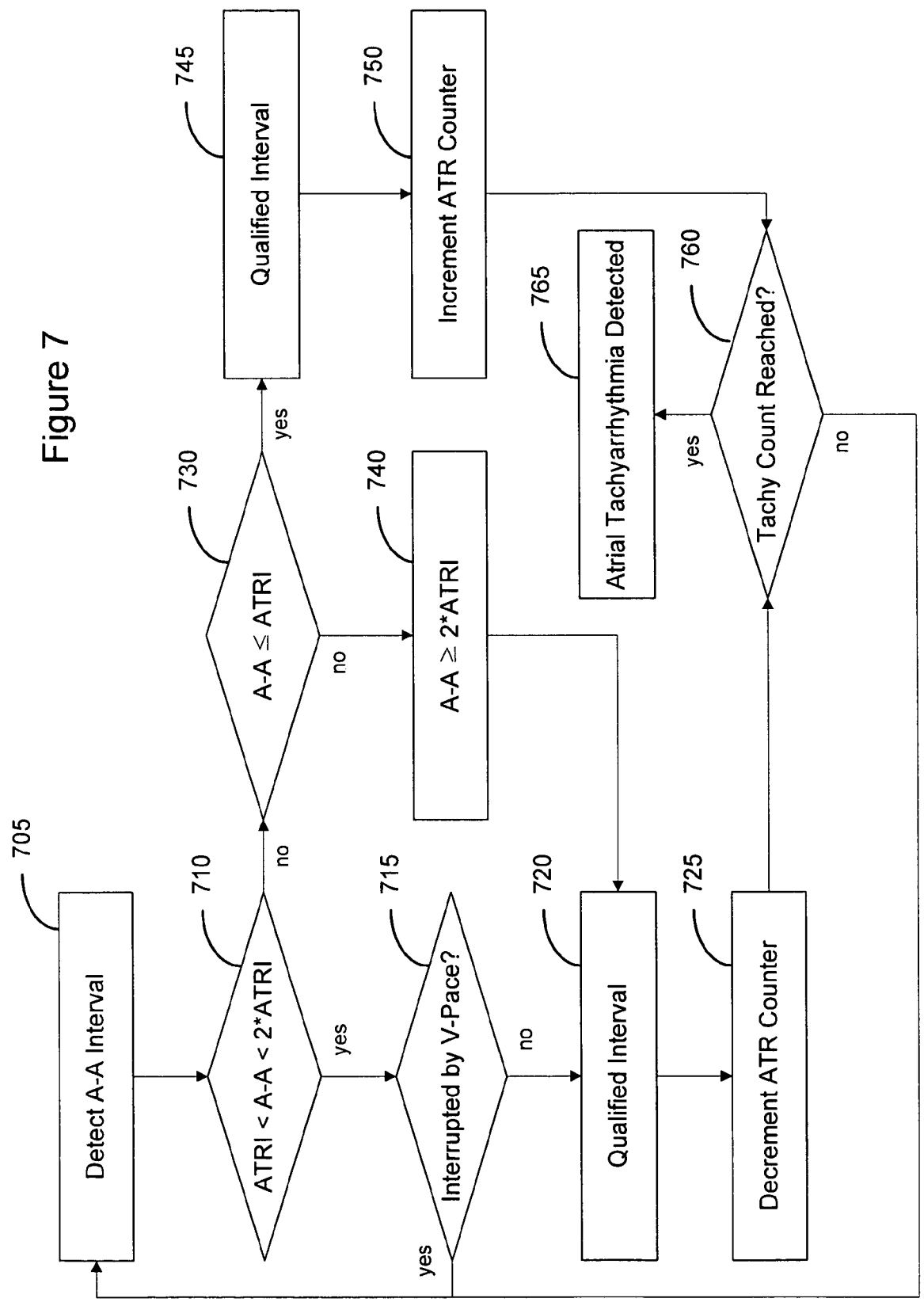

ATRIAL TACHYARRHYTHMIA DETECTION USING SELECTED ATRIAL INTERVALS

FIELD OF THE INVENTION

The present invention relates generally to implantable medical devices and, more particularly, to detecting atrial tachycardia.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, due to electrophysiologic disturbances caused by a disease process or from an electrical disturbance, the heart may experience irregularities in its coordinated contraction. In this situation, the heart is denoted to be arrhythmic. The resulting cardiac arrhythmia impairs cardiac efficiency and can be a potential life threatening event.

Cardiac arrhythmias occurring in the atria of the heart, for example, are called atrial tachyarrhythmias (ATs). ATs take many forms, including atrial fibrillation and atrial flutter. Both conditions are characterized by rapid, contractions of the atria. Cardiac arrhythmias occurring in the ventricular region of the heart, by way of further example, are called ventricular tachyarrhythmias. Ventricular tachyarrhythmias (VTs), are conditions denoted by a rapid heart beat, 150 to 250 beats per minute, originating from a location within the ventricular myocardium. Ventricular tachyarrhythmia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious tachyarrhythmias. ICDs are able to recognize and treat tachyarrhythmias with a variety of tiered therapies. These tiered therapies range from providing anti-tachycardia pacing pulses or cardioversion energy for treating tachyarrhythmias to high energy shocks for treating atrial and/or ventricular fibrillation. To effectively deliver these treatments, the ICD must first detect that a tachyarrhythmia is occurring, after which appropriate therapy may be provided to the heart.

For the reasons stated above, and for other reasons stated below which will become apparent to those skilled in the art upon reading the present specification, there is a need in the art for reliably and accurately recognizing types of cardiac rhythms produced by the heart. The present invention fulfills these and other needs.

SUMMARY OF THE INVENTION

The present invention is directed to a method and system for detecting atrial tachyarrhythmia.

In accordance with a method for detecting atrial tachyarrhythmia, a plurality of A-A intervals are detected. A-A intervals from the plurality of A-A intervals are selected and used to detect atrial tachyarrhythmia.

In various embodiment of the present invention, selecting A-A intervals includes determining if a particular A-A interval is a qualified A-A interval. Qualified A-A intervals may be determined if a duration of the particular A-A interval falls outside a predetermined duration range, for example. Qualified A-A intervals may also be determined based on events occurring between consecutively sensed atrial events of the particular A-A interval, and/or based on whether the duration of the particular A-A interval falls within the predetermined duration range. Qualified A-A intervals are selected and used to detect atrial tachyarrhythmia.

In further embodiments of the invention, qualified A-A intervals are used to detect atrial tachyarrhythmia by operating a counter using qualified A-A intervals, and detecting atrial tachyarrhythmia if the counter reaches a predetermined value.

In another embodiment of the invention, a pacing mode switch from an atrial tracking pacing mode to a non-atrial tracking pacing mode is implemented if atrial tachyarrhythmia is detected.

In yet another embodiment of the invention, a first atrial interval and a second atrial interval are detected, and the shorter A-A interval of the first and the second atrial intervals is selected.

In another embodiment of the invention, selecting the A-A intervals includes selecting odd numbered A-A intervals, and selecting even numbered A-A intervals. Detecting atrial tachyarrhythmia includes using the odd numbered intervals to increment or decrement a first counter value, and includes using the even numbered intervals to increment or decrement a second counter value. Atrial tachyarrhythmia detection is based on at least one of the first counter value and the second counter value.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 2-3 are timing diagrams illustrating undersensing of atrial events;

FIG. 4 illustrates atrial flutter with 3:1 ventricular pacing and atrial undersensing;

FIGS. 6A and 6B illustrate qualified and unqualified intervals, respectively;

FIGS. 7 and 8 are flowcharts illustrating methods of atrial tachyarrhythmia detection in accordance with embodiments of the invention;

Figure 1A:
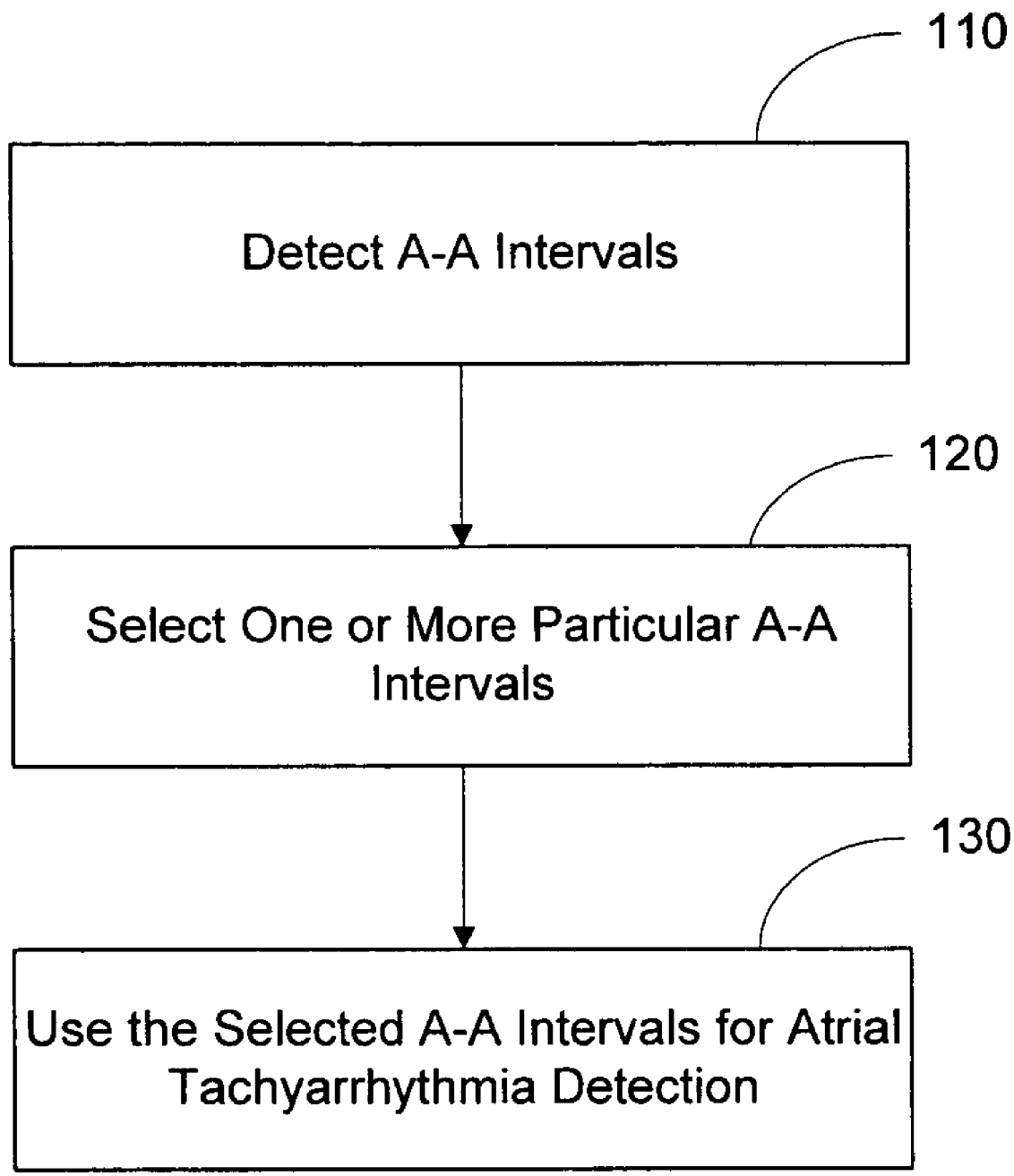
FIGS. 1A and 1B are flowcharts illustrating methods of detecting atrial tachyarrhythmia in accordance with embodiments of the invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

A cardiac rhythm management (CRM) device, such as an implantable cardiac pacemaker/defibrillator (PD), typically includes circuitry for sensing cardiac signals and for delivering electrical stimulation to one or more heart chambers. Such a device may be programmed to recognize various cardiac rhythms and provide treatment to convert, interrupt, or mitigate dangerous rhythms. A tiered approach to therapy may be implemented, wherein some rhythms are treated with a less aggressive therapy, such as anti-tachycardia pacing (ATP), other rhythms are treated with a more aggressive therapy, such as high energy cardioversion or defibrillation shocks, and some arrhythmias are left untreated.

In addition to providing the therapies described above, the CRM may also respond to tachyarrhythmias by altering pacing delivered to the patient. For example, in atrial tracking modes, a fast atrial rhythm may cause the CRM device to pace the ventricle at an inappropriately high rate. Typically, pacemakers are programmed with a maximum tracking rate (MTR) that prevents the pacemaker from delivering ventricular pacing at a rate exceeding the MTR.

In some scenarios, if the atrial rate increases beyond the MTR, the ventricular pacing rate may drop to the MTR so that a ventricular pulse is triggered by every other atrial event, for example. When the sinus tachyarrhythmia rate is greater than the MTR, the ventricular pacing may occur at a N:1 ratio with respect to atrial event.

The CRM device may respond to a detected atrial tachyarrhythmia by switching the pacing mode from an atrial tracking mode, such as DDD(R) or VDD(R) to a non-atrial tracking mode, such as DDI(R) or VDI(R). In one implementation, if the atrial rate exceeds a trigger rate, denoted the atrial tachyarrhythmia response (ATR) rate, then the mode switch occurs. Mode switching limits the amount of time ventricular pacing occurs at the maximum tracking rate. When the atrial tachyarrhythmia episode terminates, the pacing mode may be switched back to the atrial tracking mode.

Discriminating between different types of atrial arrhythmia allows the CRM device to select an appropriate therapy tailored for the particular type of arrhythmia. For example, some atrial arrhythmias are responsive to pacing therapy whereas others are more effectively treated with shock therapy. The ability to determine the type of atrial tachyarrhythmia before delivering therapy may reduce the number of shocks delivered to the patient, thus increasing the comfort of the patient and extending the device lifetime.

Detecting atrial tachyarrhythmia may involve determining if the atrial rate exceeds a threshold value. In one implementation, two or more programmable rate zones may be used for atrial tachyarrhythmia detection. If the atrial rate falls into a first rate zone, it is classified as a first type of atrial arrhythmia and a first therapy may be delivered. If the atrial rate falls into a second rate zone, the atrial arrhythmia is classified as a second type of atrial arrhythmia and a second therapy may be delivered.

In an alternate implementation, a rate threshold may be used to detect a fast atrial rate. The atrial rhythm may be further evaluated based on stability, morphology, pattern, and/or other characteristics to determine the particular type of atrial arrhythmia.

Accurate detection of atrial tachyarrhythmia involves accurate sensing of the intrinsic atrial events of an arrhythmic episode. Sensing atrial events occurring at a high rate is complicated due to post ventricular blanking periods that are implemented by the device following ventricular sensed or paced events. If atrial events fall within the post ventricular blanking periods, they may not be sensed or counted toward detection of atrial tachyarrhythmia. These unsensed atrial events cause errors in atrial tachyarrhythmia detection, in classifying the type of atrial tachyarrhythmia, and in pace mode switching. Undersensing of atrial events is exacerbated by bi-ventricular pacing which involves additional or extended blanking periods during the cardiac cycle.

Embodiments of the invention are directed to methods and systems for using sensed atrial events for atrial tachyarrhythmia detection, classification, and response. FIG. 1A is a flowchart illustrating a method of detecting atrial tachyarrhythmia in accordance with embodiments of the invention. Consecutive atrial events are sensed and intervals between the consecutively sensed A-A intervals are detected 110. One or more of the A-A intervals are selected 120. The selected A-A intervals are used 130 for atrial tachyarrhythmia detection.

Figure 1B:
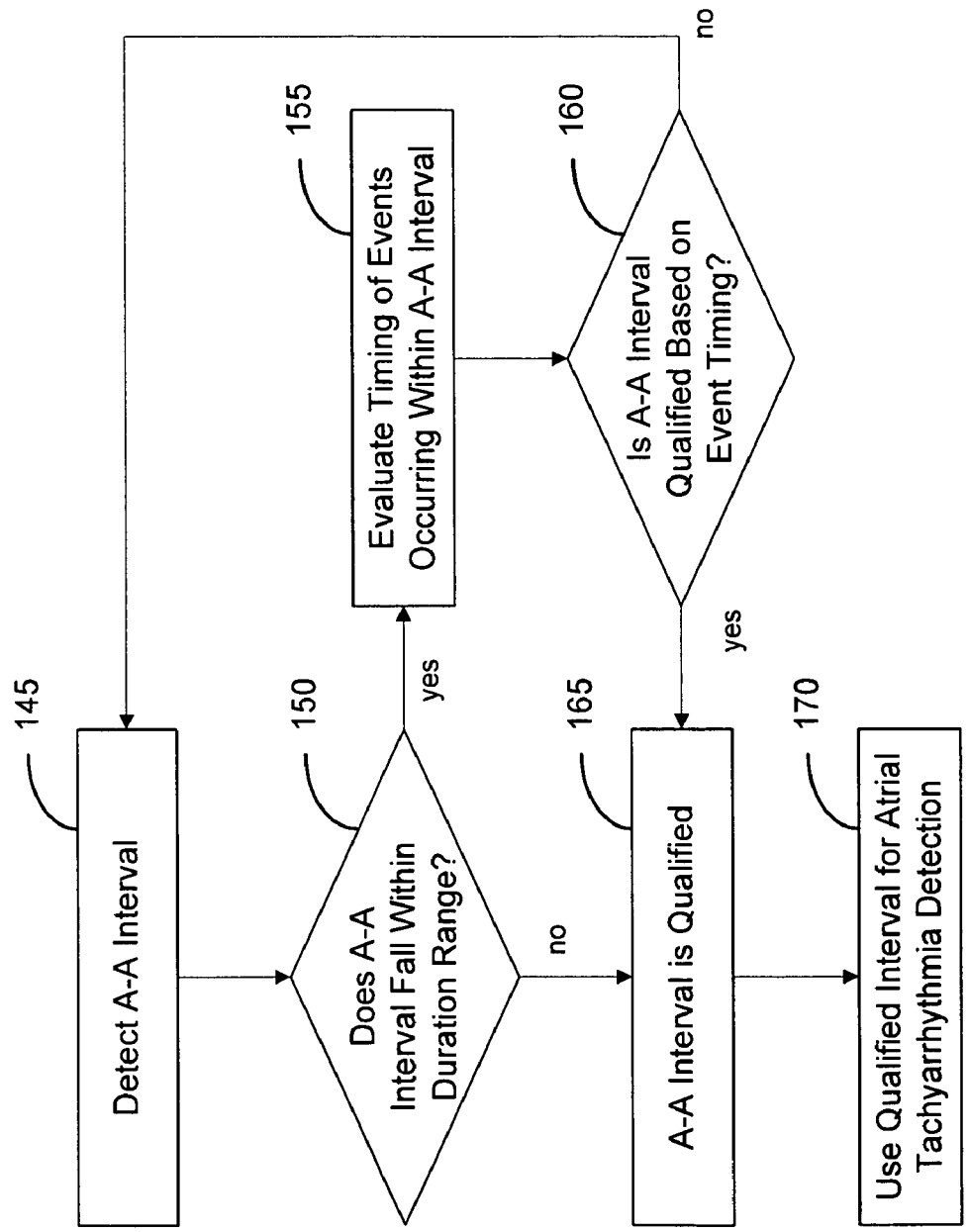

FIG. 1B is a flowchart illustrating another method of detecting atrial tachyarrhythmia in accordance with embodiments of the invention. In accordance with this method, A-A intervals are detected 145 and qualified A-A intervals are selected for atrial tachyarrhythmia detection. Determining whether or not a particular A-A interval is a qualified A-A interval includes determining 150 if the A-A interval falls within a predetermined duration range. If the A-A interval falls outside 150 the predetermined duration range, then the A-A interval is 165 a qualified interval.

If the A-A interval falls within 150 the predetermined duration range, the timing of events occurring within the A-A interval are evaluated 155. Whether or not the A-A interval is 160 a qualified A-A interval is based on the timing of events falling within the A-A interval. Qualified A-A intervals are used 170 in atrial tachyarrhythmia detection. In some implementations, a relationship between the timing of an event occurring within an A-A interval with respect to a point within the A-A interval may be used to determine if an interval is qualified. For example, an A-A interval may be determined to be qualified if the midpoint of the A-A interval does not fall within a blanking period occurring within the A-A interval.

FIGS. 2-3 are timing diagrams illustrating undersensing of atrial events. The timing diagram of FIG. 2 illustrates atrial flutter (AFL) resulting in 2:1 ventricular pacing with no undersensing of atrial events. Following the first atrial event, A1, a pacing cycle is initiated. An AV delay is initiated and the ventricle is paced, Vp, at the end of the AV delay. Following the ventricular pacing pulse, a cross chamber blanking period, PVAB, and a cross chamber refractory period, PVARP, are initiated. A second atrial event, A2, occurs during the PVARP, but after expiration of the PVAB. Thus, A2 is sensed, but is not used to initiate a pacing cycle.

The next pacing cycle is initiated by the third atrial event, A3, and is similar to the pacing cycle initiated by A1. A ventricular pacing pulse occurs after expiration of the AV delay. Cross chamber blanking and refractory periods, PVAB and PVARP, follow the ventricular pace. The next atrial event, A4, is sensed following expiration of PVAB but before expiration of PVARP. Because A4 is sensed during PVARP, A4 is not used to initiate a new pacing cycle. The pacing illustrated in FIG. 2 is representative of 2:1 behavior, wherein every other atrial event causes a pacing cycle to be initiated and the ventricle is paced at approximately one-half the atrial rate.

FIG. 3 is a timing diagram illustrating AFL producing 2:1 ventricular pacing with undersensing of atrial events. As illustrated in FIG. 3, every other atrial event is unsensed and every other atrial event initiates a pacing cycle. Following the first atrial event, A1, a pacing cycle is initiated. The ventricle is paced, Vp, at the end of the AV delay. Following Vp, a cross chamber blanking period, PVAB, and a cross chamber refractory period, PVARP, are initiated. A second atrial event, A2, occurs during PVAB. Thus, A2 is not sensed and is not used to initiate the next pacing cycle.

The second pacing cycle is initiated by the third atrial event, A3, and is similar to the pacing cycle initiated by A1. A Vp occurs after expiration of the AV delay. Cross chamber blanking and refractory periods, PVAB and PVARP, follow the ventricular pace. The next atrial event, A4, is sensed during PVAB and is not sensed.

FIG. 4 illustrates AFL with 3:1 ventricular pacing and atrial undersensing. In this situation, every other atrial event is sensed and one out of three atrial events initiates a pacing cycle. Following the first atrial event, A1, a pacing cycle is initiated. A pacing pulse, Vp, is delivered at the end of the AV delay. Following Vp, a cross chamber blanking period, PVAB, and a cross chamber refractory period, PVARP, are initiated. A second atrial event, A2, occurs during PVAB. Thus, A2 is not sensed and is not used to initiate the next pacing cycle. The next atrial event A3 is sensed during PVARP of the first pacing cycle. A3 is sensed, but is not used to start a pacing cycle.

The next pacing cycle is initiated by the fourth atrial event, A4, and is similar to the pacing cycle initiated by A1. A Vp is delivered after expiration of the AV delay. Cross chamber blanking and refractory periods, PVAB and PVARP, follow the ventricular pace. A5 is sensed during PVAB and is not sensed nor used to start a pacing cycle. A6 is sensed during PVARP and is sensed, but is not used to start a pacing cycle.

Figure 5:
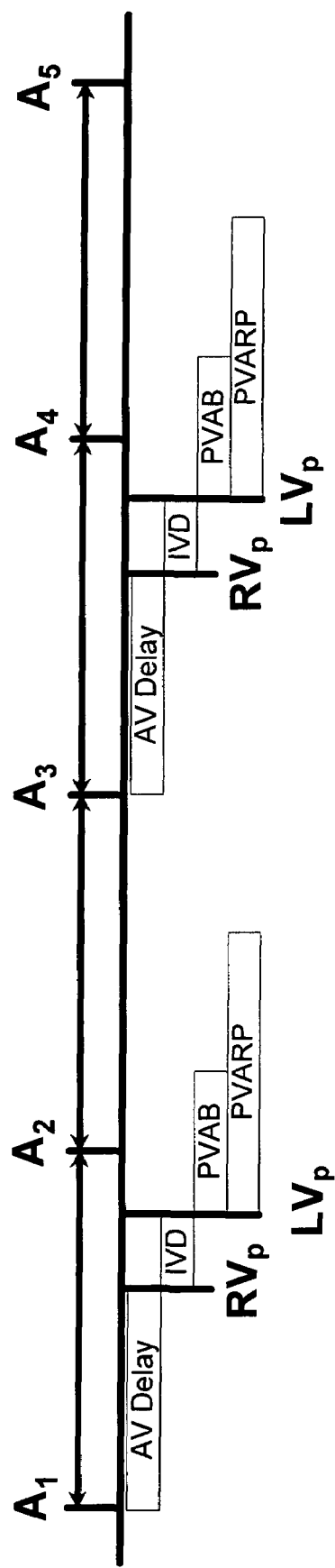
FIG. 5 illustrates atrial event undersensing during bi-ventricular pacing.

FIG. 5 illustrates atrial event undersensing during bi-ventricular pacing. A sensed atrial event that does not fall within a PVARP is used to initiate an AV delay for a cardiac pacing cycle. If the right ventricle is paced, RVp, following the AV delay, the opposite ventricle is paced, LVp, following an interventricular delay (IVD). A PVAB period and a PVARP are initiated by the left ventricular pace. Thus, when bi-ventricular pacing is delivered, post ventricular blanking in the atrium is increased by the interventricular delay (IVD) which may have a duration of up to about 100 ms.

Detection of atrial tachyarrhythmia involves counting the number of A-A intervals that fall into one or more atrial tachyarrhythmia rate zones. Undersensing of atrial events, as illustrated in the examples of FIGS. 3-5, may cause failure or delays in satisfying rate zone detection counters used in detection of atrial tachyarrhythmia. Further, the long A-A intervals caused by atrial undersensing may cause errors in the classification of types of atrial tachyarrhythmia, e.g., atrial fibrillation vs. atrial flutter. Further, undersensed atrial events may cause delays in implementation of atrial tachyarrhythmia therapy or inappropriate mode switching. For example, atrial undersensing may cause delays in mode switching or oscillations in switching back and forth between tracking mode and non-tracking mode. As described below in accordance with various exemplary embodiments, the problems associated with atrial undersensing may be reduced by using qualified intervals for atrial tachyarrhythmia detection and/or classification.

In one implementation of atrial tachyarrhythmia detection, the device uses one or more counters to determine the number of fast atrial events occurring within a rate zone detection window. For example, a rate zone detection window may be satisfied if x out of y, e.g., about 32 out of about 40, of the most recent A-A intervals are short A-A intervals, corresponding to a high atrial rate. After the detection window is satisfied, then it will remain satisfied if a predetermined number e.g., about 24 out of about 40, of the most recent A-A intervals are short atrial intervals.

The device compares each detected A-A interval to a predetermined interval value, denoted the atrial tachyarrhythmia response interval (ATRI), associated with a fast atrial rate. The rate zone counter is incremented if a detected A-A interval is shorter than the ATRI and is decremented if a detected A-A interval is longer than the ATRI. When the counter reaches a predetermined value, then an atrial tachyarrhythmia episode is detected. Additional short A-A intervals may be used to confirm the atrial tachyarrhythmia episode. During the atrial tachyarrhythmia episode, the counter is incremented by short intervals and decremented by long intervals as before. If the counter value reaches zero, the atrial tachyarrhythmia episode is determined to have terminated.

The use of only qualified atrial intervals to increment or decrement the atrial detection counter may allow reliable detection of atrial arrhythmias. For example, using qualified atrial intervals, the detection window may be satisfied if about 24 out of about 30 or if about 16 out of about 20 are shorter than the ATRI.

In accordance with one embodiment of the invention, the following A-A intervals are considered to be qualified atrial intervals:

Qualified A-A Interval Criteria Set 1
1) A-A<ATRI, even though interrupted by a ventricular pace;
2) A-A>N×ATRI, where N is about 2; and
3) ATRI<A-A<N×ATRI and the A-A interval is not interrupted by a ventricular pace.

The above qualified A-A interval criteria set may be used if the device is not able to discern the timing of a PVAB that falls within the A-A interval. In some implementations, the device may be able to determine the timing of the PVAB with respect to a PVAB falling within the A-A interval. If so, then the criteria for qualified A-A intervals may be modified as follows:

Qualified A-A Interval Criteria Set 2
1) A-A<ATRI, even though interrupted by a ventricular pace;
2) A-A>N×ATRI, where N is about 2;
3) ATRI<A-A<N×ATRI and the A-A interval is not interrupted by a ventricular pace
4) ATRI<A-A<N×ATRI and the midpoint of A-A interval does not occur during PVAB.

FIGS. 6A and 6B illustrate qualified and unqualified intervals, respectively, according to criterion 4 above. FIG. 6A, illustrates qualified A-A intervals having midpoints that do not fall within PVAB. FIG. 6B illustrates unqualified A-A intervals that have midpoints that fall within PVAB.

In yet another embodiment, the following criteria may be used to identify qualified A-A intervals:

Qualified A-A Interval Criteria Set 3
1) A-A<ATRI, even though interrupted by a ventricular pace;
2) A-A>N×ATRI, where N is about 2;
3) ATRI<A-A<N×ATRI and the A-A interval is not interrupted by a ventricular pace; and
4) ATRI<A-A<N×ATRI and both of the following:
   the midpoint of A-A interval does not occur during PVAB;
   A to Vp greater than ATRI or Vp to A greater than ATRI+PVAB.

The criteria sets described above are provided as example criteria sets. Criteria sets for identifying qualified A-A intervals may include additional criteria or alternative criteria to those presented in the examples above.

FIG. 7 is a flowchart illustrating a method of atrial tachyarrhythmia detection in accordance with embodiments of the invention. The method illustrated in FIG. 7 corresponds to Criteria Set 1, above. Atrial events are sensed and A-A intervals between consecutively sensed atrial events are detected 705. If the length of the atrial interval is 710 between the ATRI and twice the ATRI and the A-A interval is not interrupted 715 by a ventricular pace, then the A-A interval is 720 a qualified long A-A interval and is used 725 to decrement the ATR counter. If the length of the atrial interval is 710 between the ATRI and twice the ATRI and the A-A interval is not interrupted 715 by a ventricular pace, then the A-A interval is not a qualified A-A interval. The unqualified A-A interval is not used for atrial tachyarrhythmia detection and the next A-A interval is detected 705.

If the A-A interval is less than or equal to 730 the ATRI, then the A-A interval is 745 a qualified short interval and it is used to increment 750 the ATR counter. If the A-A interval is greater than or equal to 740 twice the ATRI, then the A-A interval is 720 a qualified long interval and is used to decrement 725 the ATR counter. If the ATR counter value reaches 760 a predetermined value, then atrial tachyarrhythmia is detected 765.

Figure 8:
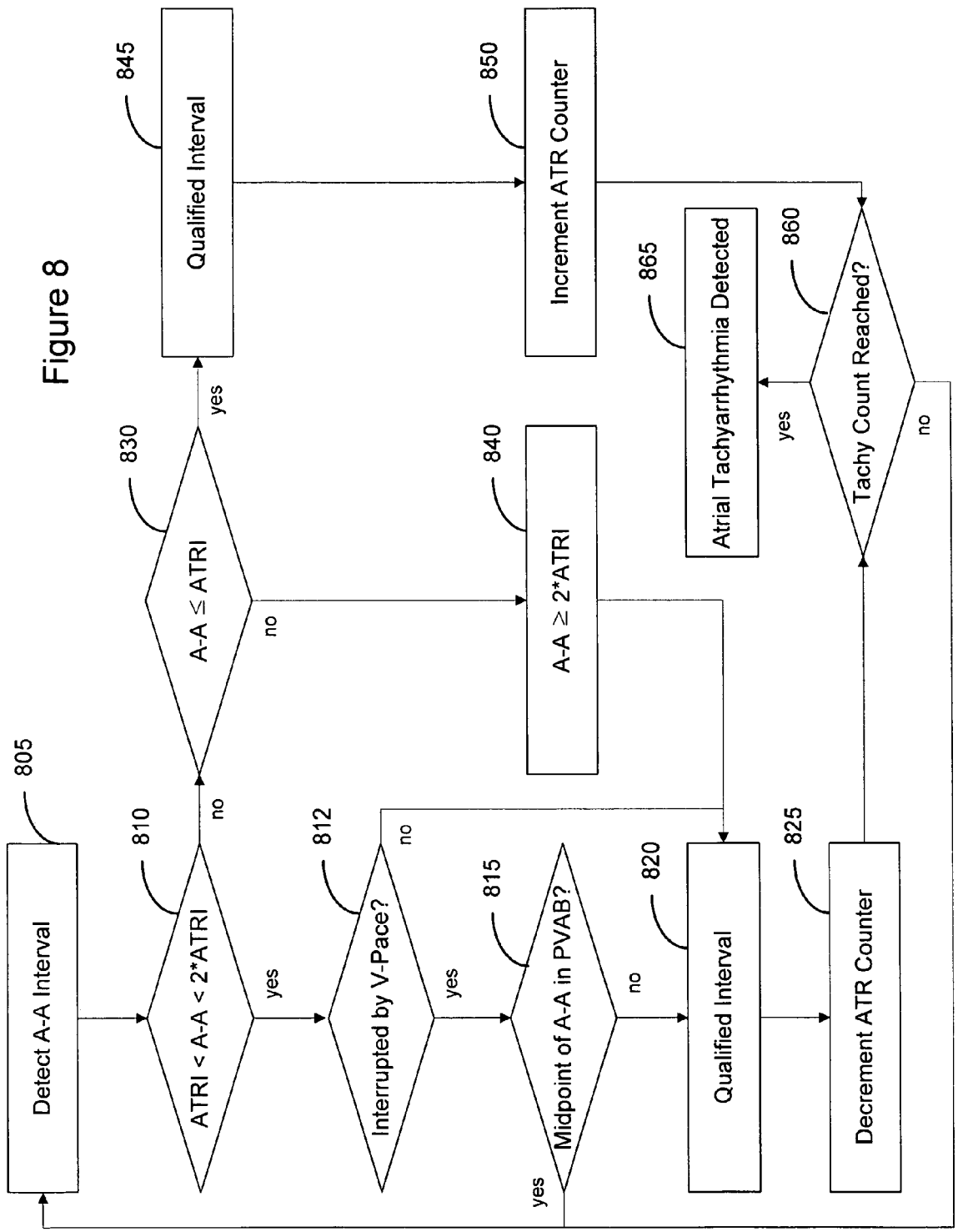

FIG. 8 is a flowchart illustrating a method of atrial tachyarrhythmia detection in accordance with embodiments of the invention. The method illustrated in FIG. 8 corresponds to Criteria Set 2, above. Atrial events are sensed and A-A intervals between consecutively sensed atrial events are detected 805. If the length of the A-A interval is 810 between the ATRI and twice the ATRI and the A-A interval does not include 812 a ventricular pace, then the A-A interval is a qualified long interval 820 and is used to decrement the ATR counter.

If the A-A interval is 810 between the ATRI and twice the ATRI and the A-A interval and the A-A interval includes 812 a ventricular pace the A-A interval is a qualified long interval 820 if the midpoint of the A-A interval does not fall 815 within a blanking period. The A-A interval and is used 825 to decrement the ATR counter. If the length of the atrial interval is 810 between the ATRI and twice the ATRI and the midpoint of the A-A interval falls within 815 a blanking period, then interval is not used for tachyarrhythmia detection and the system detects 805 the next interval.

If the A-A interval is less than or equal to 830 the ATRI, then the A-A interval is 845 a qualified short interval and it is used to increment 850 the ATR counter. If the A-A interval is greater than or equal to 840 twice the ATRI, then the A-A interval is a qualified long interval 820 and is used to decrement 825 the ATR counter. If the ATR counter value reaches 860 a predetermined value, then atrial tachyarrhythmia is detected 865.

Figure 9:
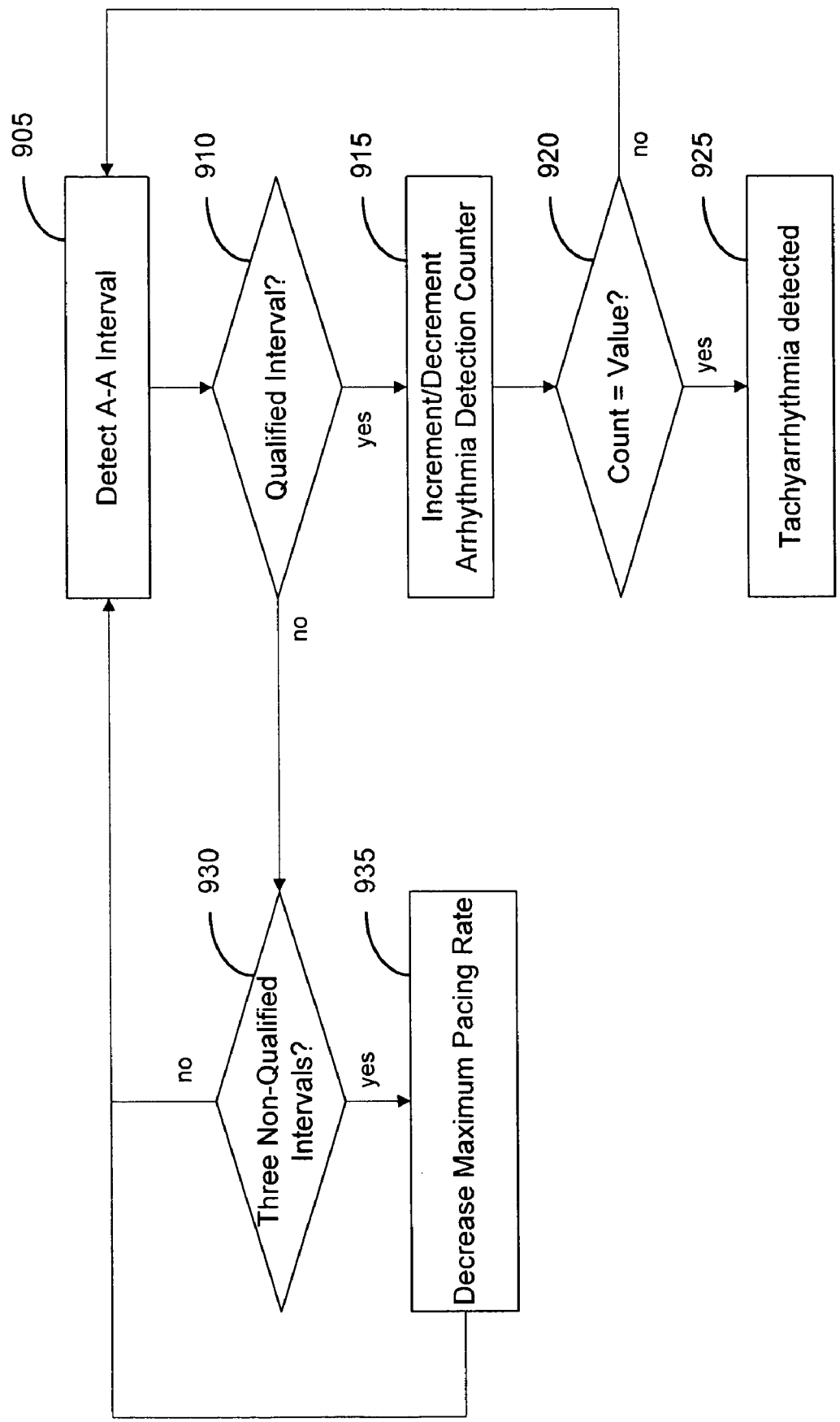
FIG. 9 illustrates a method of increasing the number of qualified A-A intervals in accordance with embodiments of the invention.

In some scenarios, the number of qualified A-A intervals occurring within a time period may not be sufficient for to detect arrhythmia, classify the arrhythmia and/or determine an appropriate response to the arrhythmia. In these situations, additional processes may be implemented to mitigate undersensing of atrial events to increase the number of qualified A-A intervals, or to otherwise enhance arrhythmia detection, classification, and/or response processes. FIG. 9 illustrates a method of increasing the number of qualified A-A intervals in accordance with embodiments of the invention. Atrial events are sensed and A-A intervals are detected 905. Qualified atrial intervals 910 are used to increment or decrement 915 an atrial tachyarrhythmia detection counter as described in connection with the examples above. When the counter value reaches 920 a predetermined value, then atrial tachyarrhythmia is detected 925.

If a predetermined number of sequential non-qualified A-A intervals, for example, about 3 non-qualified A-A intervals, are detected 930, processes to reduce atrial undersensing may be initiated. In one embodiment, reducing atrial undersensing involves decreasing 935 the maximum pacing rate, for example by about 10 bpm. Decreasing the maximum pacing rate may increase the number of qualified intervals available for tachyarrhythmia detection.

As previously discussed, if atrial tachyarrhythmia is detected, the device may switch the pacing mode from an atrial tracking mode to a non-tracking mode. Pacing continues in the non-tracking mode for a period of time or so long as the atrial tachyarrhythmia is present. After the atrial rate drops, the device may switch back to the atrial tracking pacing mode.

Figure 10:
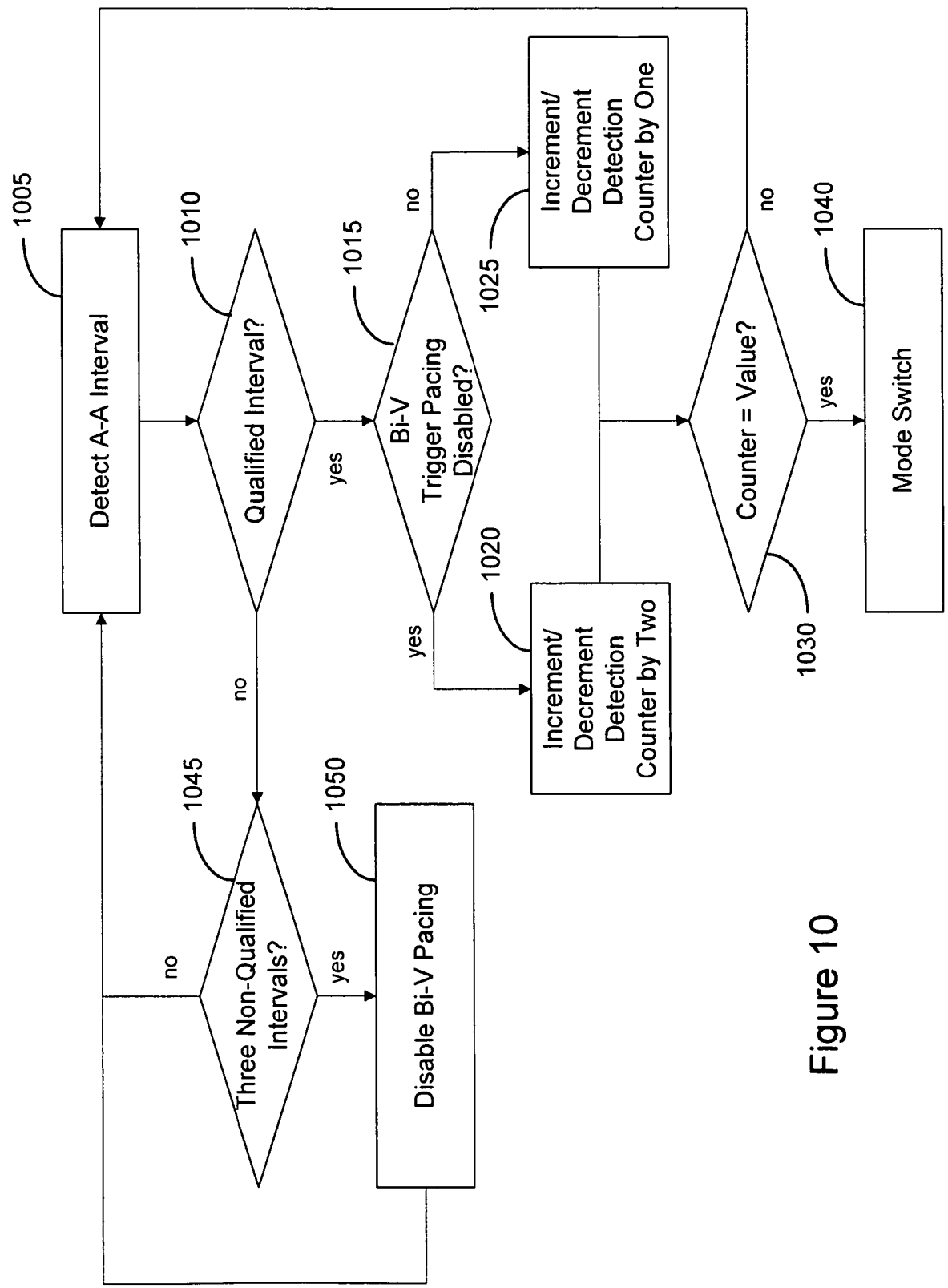
FIG. 10 is a flowchart illustrating a method of implementing a pacing mode change from an atrial tracking mode to a non-tracking mode in accordance with embodiments of the invention.

FIG. 10 is a flowchart illustrating a method of implementing a pacing mode change from an atrial tracking mode to a non-tracking mode in accordance with embodiments of the invention. A-A intervals are detected 1005 and a determination is made as to whether the A-A intervals are qualified 1010. In instances where three consecutive unqualified A-A intervals occur 1045, then bi-ventricular pacing is disabled 1050 for a number of beats, e.g., about one beat. For a qualified interval 1010, and if bi-ventricular trigger pacing is not disabled 1015, each qualified A-A interval increments or decrements 1025 the atrial tachyarrhythmia counter by one. For a qualified interval 1010 with bi-ventricular trigger pacing disabled 1015, each qualified A-A interval increments or decrements 1020 the atrial tachyarrhythmia detection counter by a predetermined number, e.g., about 2. When the atrial tachyarrhythmia counter reaches 1030 a predetermined value, then a mode switch occurs 1040 from the atrial tracking mode to the non-tracking mode.

Figure 11:
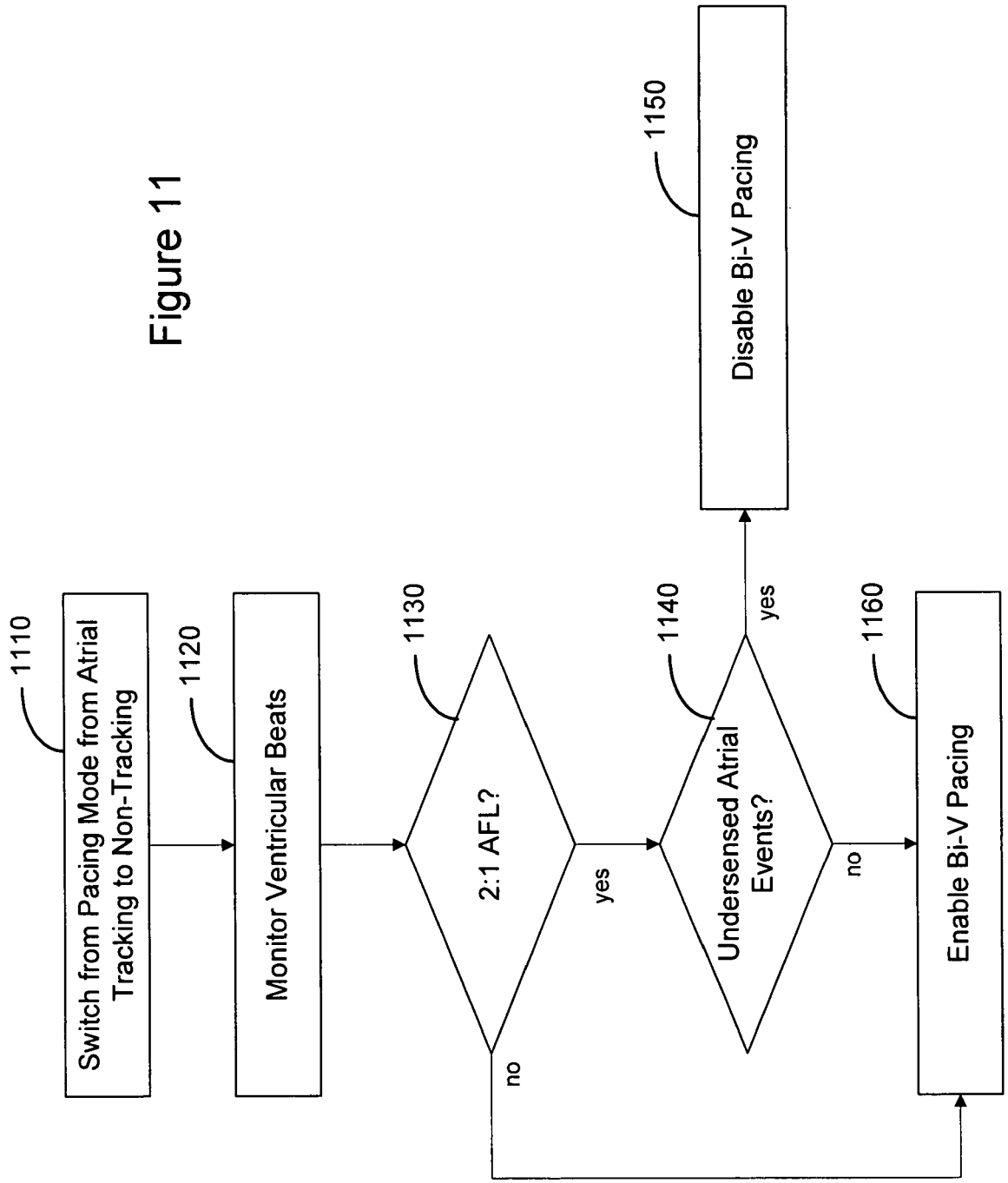
FIG. 11 is a flowchart illustrating a method of implementing a bi-ventricular pacing therapy after a pacing mode switch from an atrial tracking mode to a non-tracking mode in accordance with embodiments of the invention.

FIG. 11 is a flowchart illustrating a method of implementing a bi-ventricular pacing therapy after a pacing mode switch 1110 from an atrial tracking mode to a non-tracking mode in accordance with embodiments of the invention. Several ventricular beats, e.g., about eight beats are monitored 1120 to determine the consistency of the conduction pattern. If 1130 the rhythm is not 2:1 AFL, bi-ventricular pacing is enabled. If 1130 the rhythm is 2:1 AFL, prior to enabling bi-ventricular trigger pacing, the system determines if bi-ventricular trigger pacing will cause 1140 undersensing of atrial events. If undersensed atrial events would not 1140 occur during bi-ventricular trigger pacing, then bi-ventricular trigger pacing is enabled 1160. If undersensed atrial events would 1140 occur during bi-ventricular trigger pacing, then bi-ventricular trigger pacing may be disabled 1150 until after atrial therapy is delivered.

Figure 12:
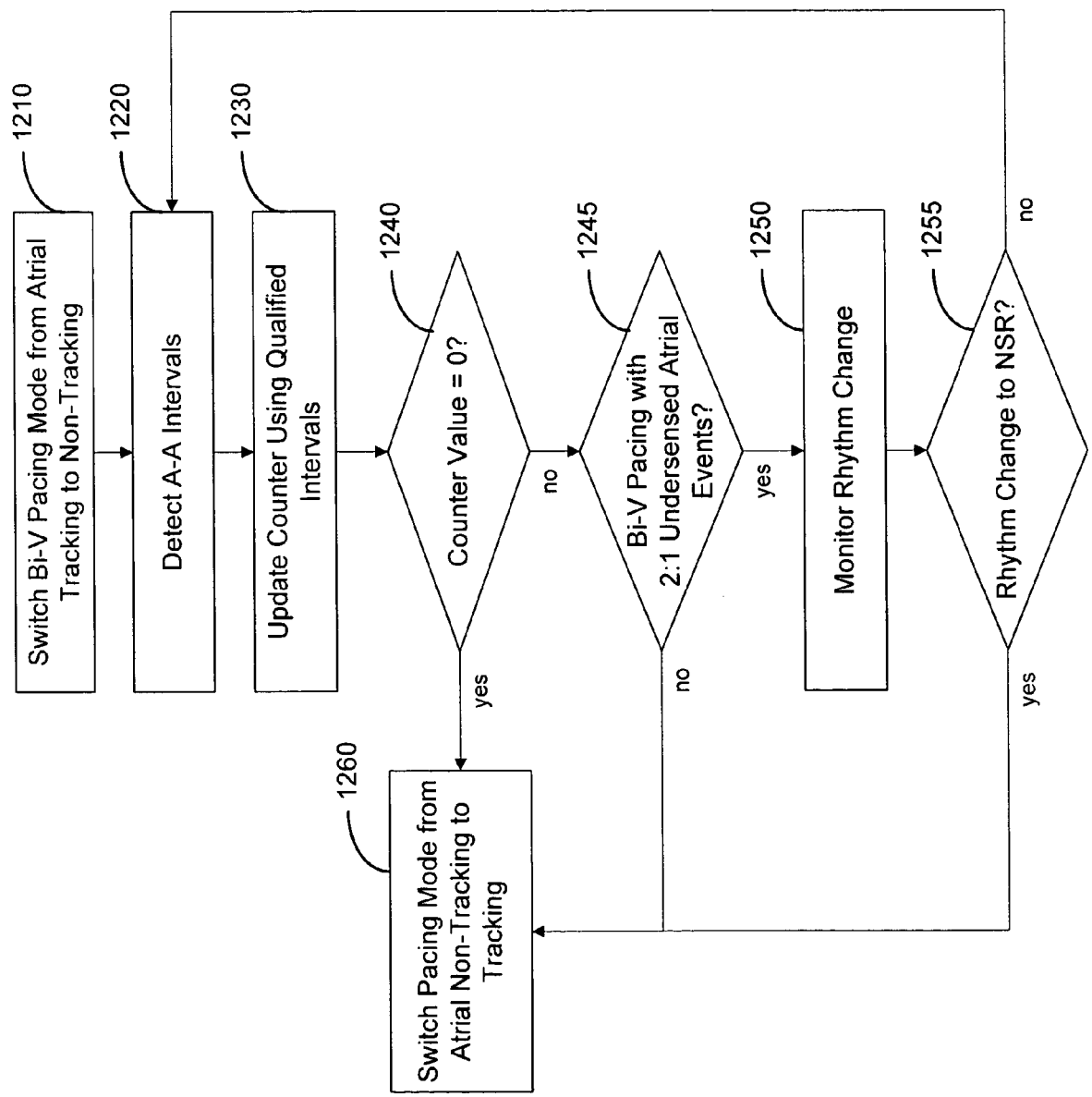
FIG. 12 illustrates a method of implementing a pacing mode switch from a non-tracking mode to an atrial tracking mode in accordance with embodiments of the invention.

As previously discussed, detection of an atrial tachyarrhythmia may cause a pacing mode switch from an atrial tracking mode to a non-tracking mode. When the atrial tachyarrhythmia subsides, then the pacing mode may be switched back to tracking mode. FIG. 12 illustrates a method of implementing a pacing mode switch from a non-tracking mode to an atrial tracking mode in accordance with embodiments of the invention. Following a pacing mode change 1210 to a non-tracking mode, A-A intervals are detected 1220. An atrial tachyarrhythmia counter is updated 1230 (incremented or decremented) using qualified A-A intervals. Updating the detection counter involves incrementing the counter if a short qualified A-A interval is detected and decrementing the counter if a long qualified A-A interval is detected. When the counter value reaches 1240 zero, a sufficient number of long qualified A-A intervals have occurred within the detection window to determine that the atrial tachyarrhythmia has subsided. The pacing mode is switched 1260 from the non-tracking mode to an atrial tracking mode.

If the current rhythm is 1245 undersensed 2:1 AFL and bi-ventricular pacing is being delivered, then a rhythm change is monitored 1250 while the counter non-zero. If a rhythm change to normal sinus rhythm is detected 1255 then the pacing mode is switched 1260 from the non-tracking mode to atrial tracking.

Figure 13:
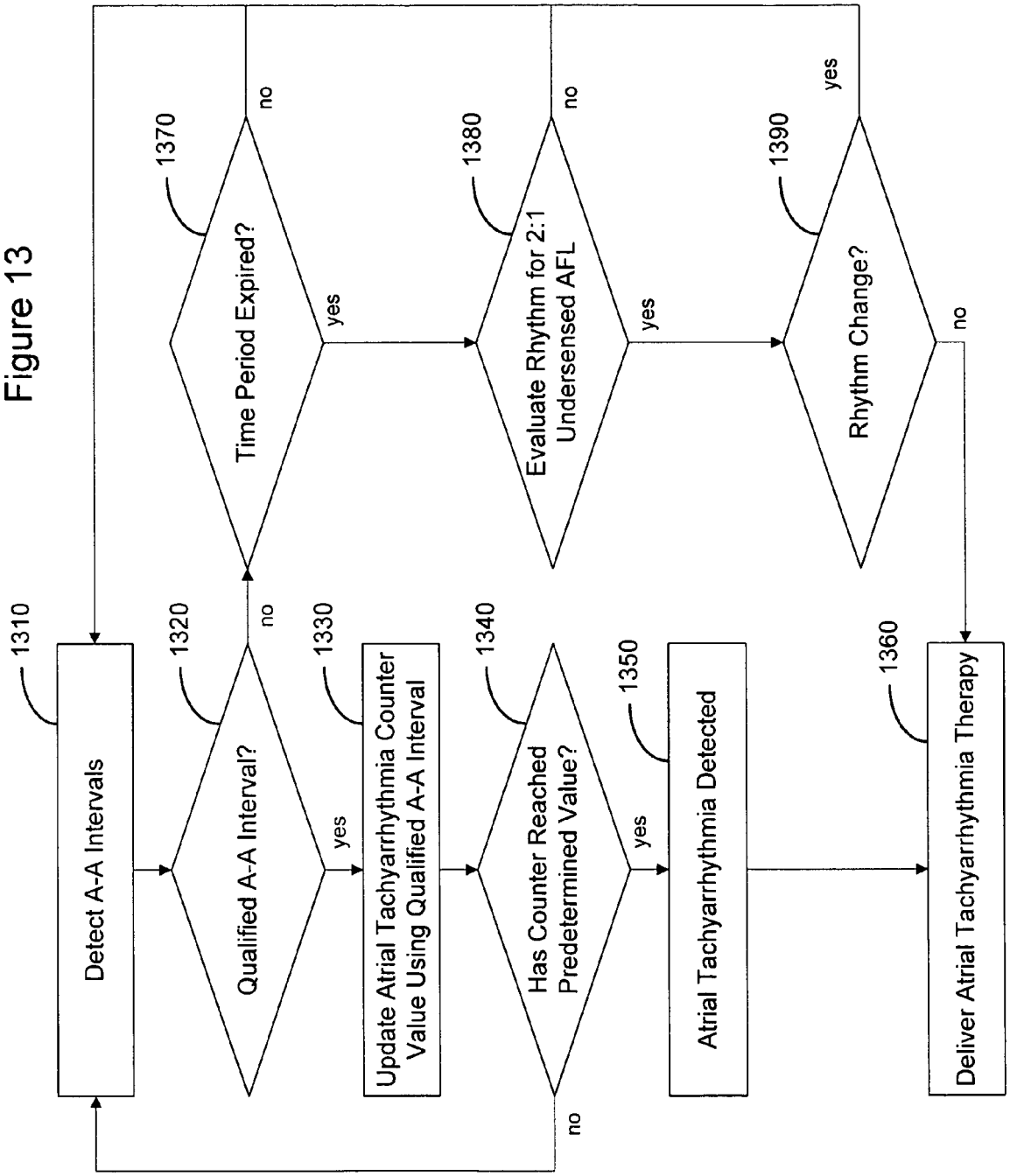
FIG. 13 illustrates a method in accordance with embodiments of the invention for detecting atrial tachyarrhythmia and delivering therapy.

In some circumstances, a lack of qualified A-A intervals in a tachyarrhythmia episode may cause delays in atrial tachyarrhythmia detection and therapy delivery. FIG. 13 illustrates a method in accordance with embodiments of the invention for detecting atrial tachyarrhythmia and delivering therapy. In accordance with this method, A-A intervals are detected 1310 and qualified A-A intervals 1320 are used to update 1330 the atrial tachyarrhythmia detection counter. If the counter reaches 1340 a predetermined value, indicating the presence of atrial tachyarrhythmia, then atrial tachyarrhythmia is detected 1350 and therapy is delivered 1360.

If a sufficient number of qualified A-A intervals are not detected 1320 within a predetermined time period 1370, for example, about 30 seconds, then further processing 1380, 1390 occurs to determine if therapy should be delivered. The rhythm is evaluated 1380 and if the current rhythm is 2:1 undersensed AFL, then the device checks to see if a rhythm change has occurred 1390. If a rhythm change is not detected 1390, then atrial tachyarrhythmia therapy is delivered 1360. If a rhythm change is detected 1390, then the device continues to detect A-A intervals 1310 for atrial tachyarrhythmia detection.

In some implementations, the system may classify the type of arrhythmia that is occurring. Classifying the type of atrial tachyarrhythmia may be useful in selecting an appropriate therapy to treat the arrhythmia. For example, some atrial arrhythmias, such as atrial flutter, are pace terminable, whereas other atrial arrhythmias, such as atrial fibrillation, are more effectively treated using shocks.

Figure 14:
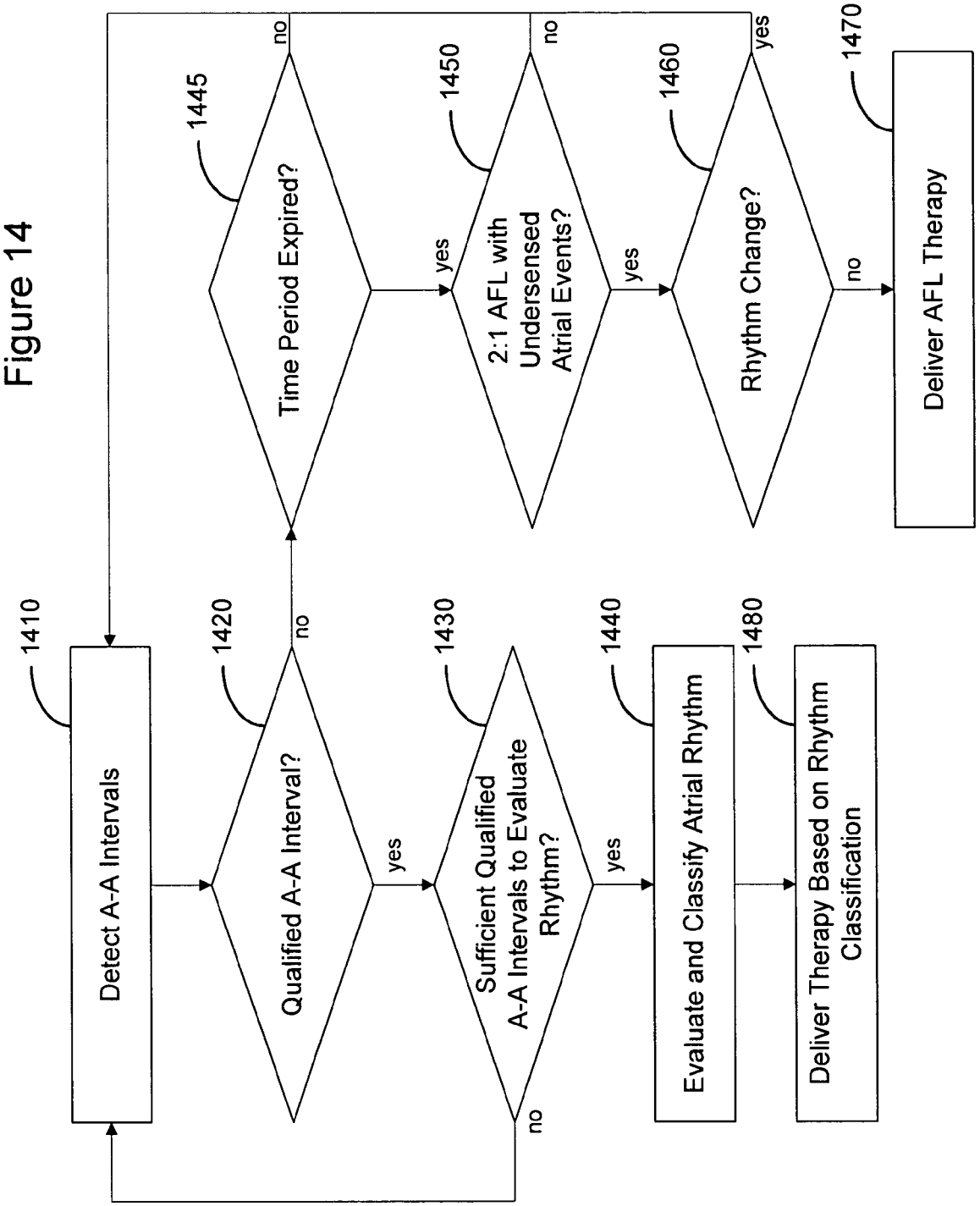
FIG. 14 is a flowchart illustrating a method of using qualified A-A intervals for classifying atrial tachyarrhythmia.

In some embodiments, qualified A-A intervals are used to classify the type of atrial arrhythmia that is occurring. FIG. 14 is a flowchart illustrating a method of using qualified A-A intervals for classifying atrial tachyarrhythmia. According to this embodiment, an A-A interval is detected 1410 and the system determines 1420 if the detected A-A interval is a qualified A-A interval. If a sufficient number of qualified A-A intervals have been acquired 1430, then the qualified A-A intervals are used to evaluate the rhythm. The rhythm is evaluated 1440 and the type of atrial rhythm is classified using the qualified A-A intervals. An appropriate therapy may be delivered 1480 based on the atrial rhythm classification.

If the detected A-A interval is 1420 not qualified, then the system determines if a sufficient number of qualified A-A intervals are detected 1445 within a predetermined time period, for example, about 30 seconds. Where the time period has not expired 1445, A-A intervals continue to be detected. Where the time period has expired, a determination 1450 is made as to whether the atrial rhythm is 2:1 AFL with undersensed atrial events. If 2:1 AFL with atrial event undersensing is determined 1450 to be present, then the system determines 1460 if rhythm change has occurred. If a rhythm change is not detected, then AFL therapy is delivered 1470. If a rhythm change is detected, or if the current rhythm is determined 1450 not to be 2:1 AFL with atrial event undersensing, then classification of the rhythm is delayed until a sufficient number of qualified A-A intervals are acquired.

Figure 15:
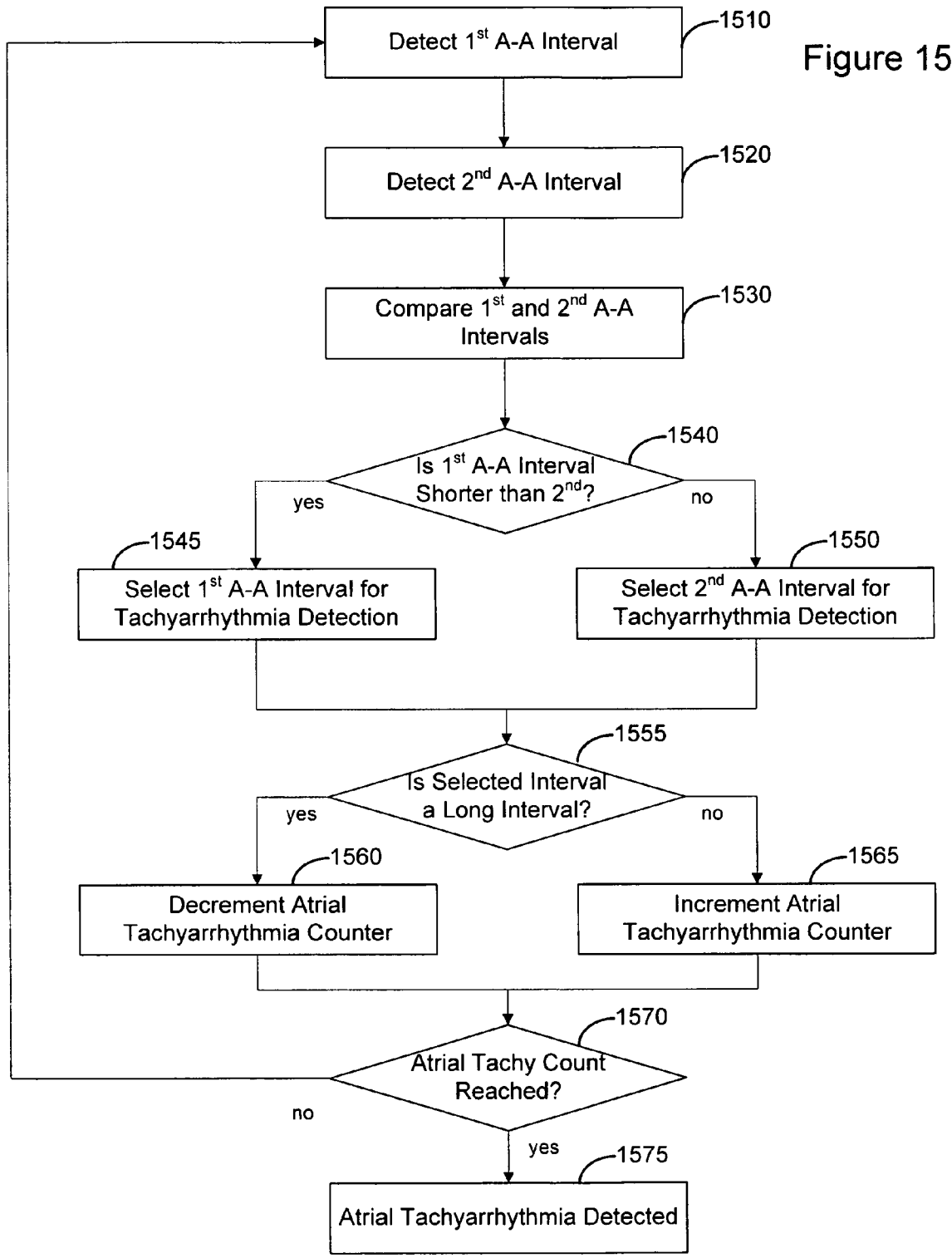
FIG. 15 illustrates a method for detecting atrial tachyarrhythmia in accordance with embodiments of the invention.

Processes described above involve selecting qualified A-A intervals for atrial tachyarrhythmia detection. In accordance with some embodiments of the invention, the selection of A-A intervals may not be evaluated to determine if the A-A intervals are consistent with qualifying criteria, such as the exemplary qualified A-A interval criteria sets described above. A method for detecting atrial tachyarrhythmia in accordance with embodiments of the invention, is illustrated in the flowchart of FIG. 15. According to this method two sequential A-A intervals are detected and the shortest of the two A-A intervals is used to update the atrial tachyarrhythmia detection counter. This method provides more sensitive and stable atrial tachyarrhythmia detection and response.

As illustrated in FIG. 15, first and second A-A intervals are detected 1510, 1520. The duration of the first A-A interval is compared 1530 to the duration of the second A-A interval. If the first A-A interval is shorter than 1540 the second A-A interval, then the first A-A interval is selected 1545 for use in atrial tachyarrhythmia detection. If the second A-A interval is shorter than 1540 the first A-A interval, then the second A-A interval is selected 1550 for use in atrial tachyarrhythmia detection.

The duration of the selected interval is compared to the duration of a detection interval. If the selected interval is longer than 1555 the duration of detection interval, the selected A-A interval is a long A-A interval. Long A-A intervals are used to decrement 1560 the atrial tachyarrhythmia counter. If the selected interval is shorter than 1555 the duration of detection interval, then the selected interval is a short A-A interval. Short A-A intervals are used to increment 1565 the atrial tachyarrhythmia counter. After incrementing 1565 or decrementing 1560 the atrial tachyarrhythmia counter, a determination 1570 about whether the atrial tachyarrhythmia window is satisfied 1570, e.g., if x out of y A-A intervals are short A-A intervals. When satisfied, atrial tachyarrhythmia is detected 1575. Otherwise, the process re-starts with a first A-A interval detection 1510.

Figure 16A:
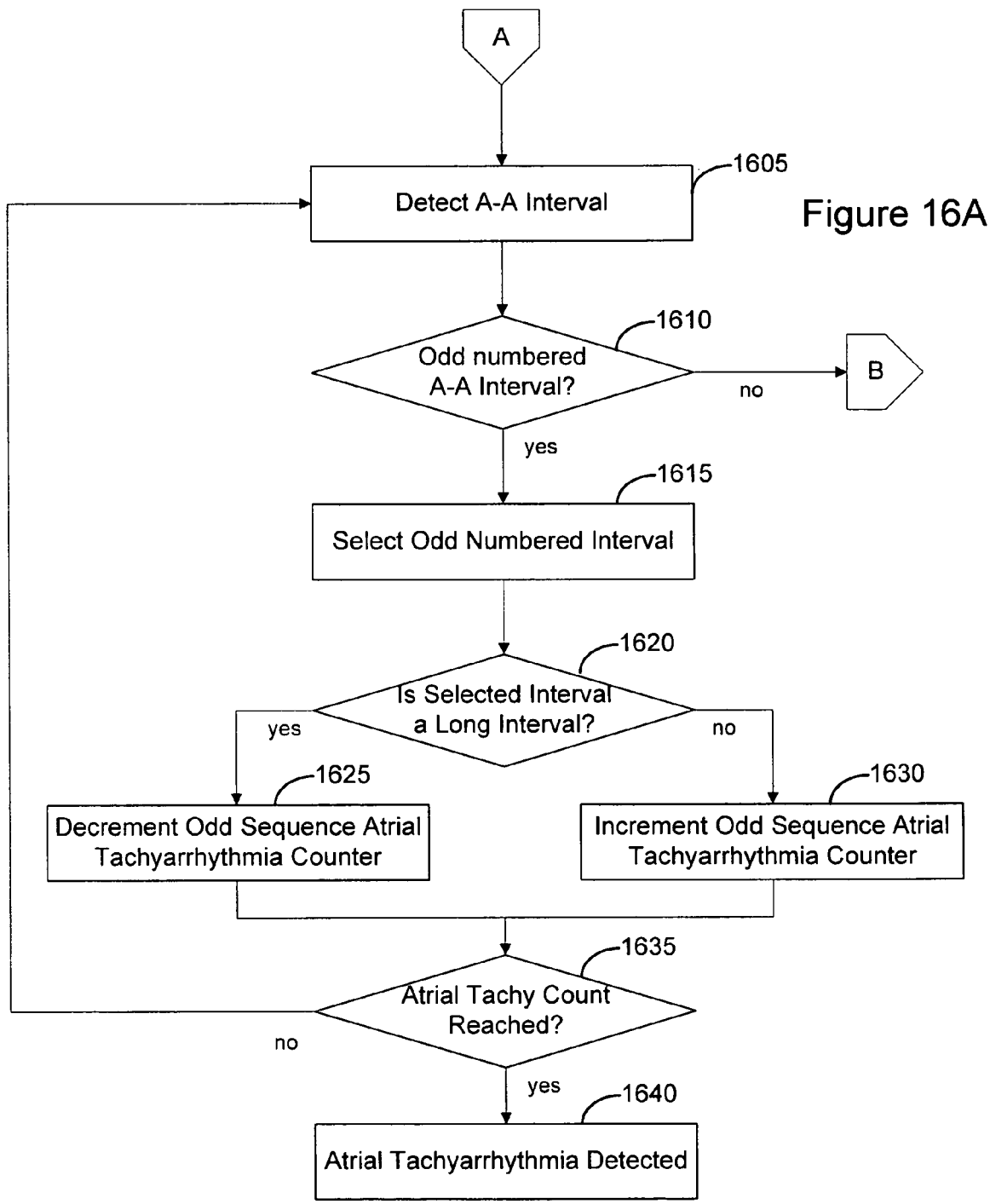
FIGS. 16A and 16B illustrate two counters used for detection of atrial tachyarrhythmia, in accordance with another embodiment of the invention.
Figure 16B:
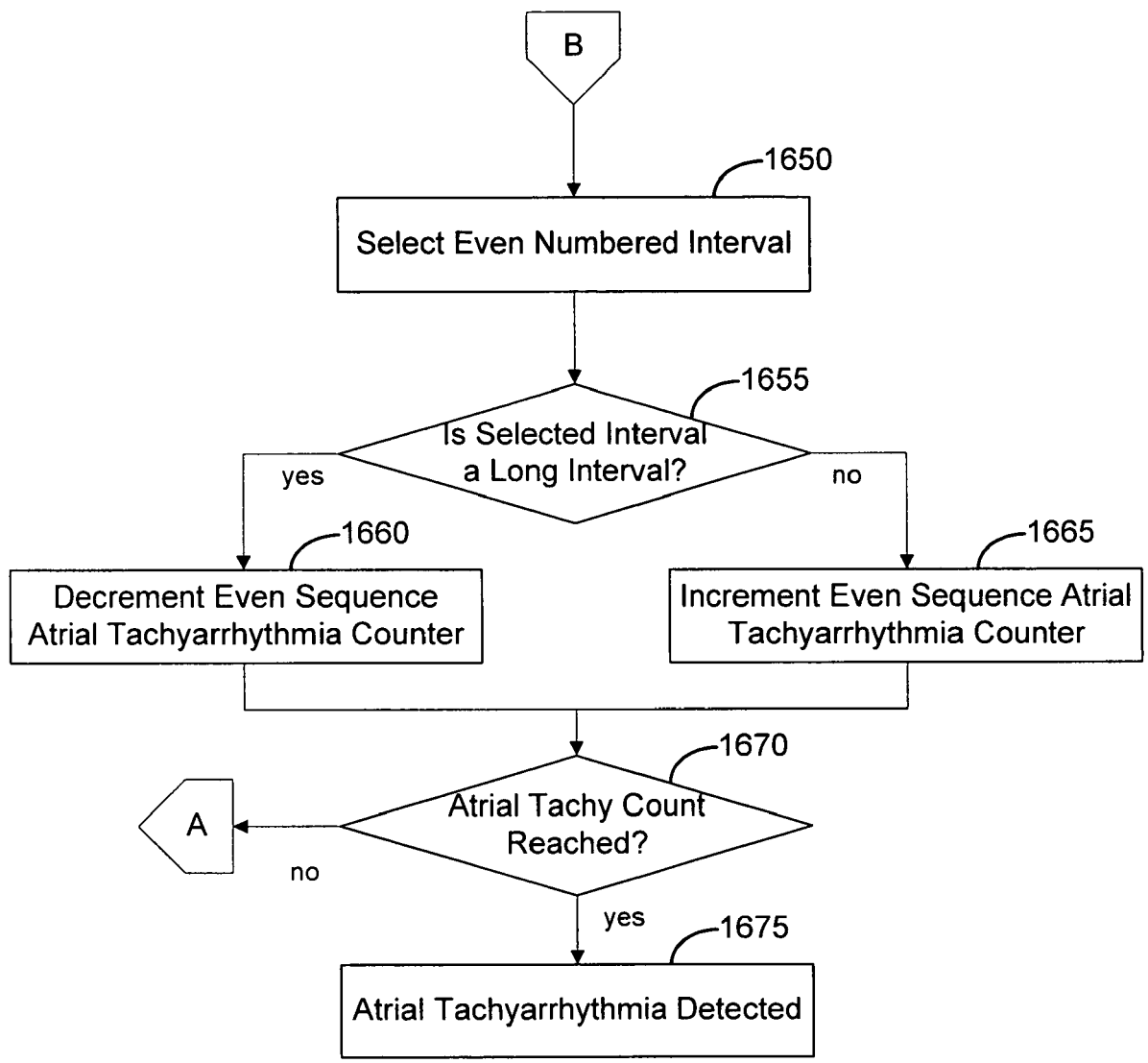

In accordance with another embodiment of the invention, FIGS. 16A and 16B illustrate two counters used for detection of atrial tachyarrhythmia. Odd numbered A-A intervals, e.g., $1^{st}$, $3^{rd}$, $5^{th}$, etc. detected A-A intervals, are used to operate a first counter. Even numbered A-A intervals, e.g., $2^{nd}$, $4^{th}$, $6^{th}$, etc., detected A-A intervals, are used to operate the second counter. If either the first or the second counters reach a predetermined count, atrial tachyarrhythmia is detected.

According to the method as illustrated in the flowchart of FIGS. 16A and 16B, an A-A interval is detected 1605 and the system ascertains whether the A-A interval is an odd or even numbered interval in the sequence. If the A-A interval is 1610 an odd numbered interval in the sequence, then the odd numbered A-A interval is selected 1615 to operate the odd sequence atrial tachyarrhythmia counter.

The duration of the selected interval is compared to the duration of a detection interval. If the selected interval is longer than 1620 the duration interval, the selected A-A interval is a long A-A interval. Long A-A intervals are used to decrement 1625 the odd sequence atrial tachyarrhythmia counter. If the selected interval is shorter than 1620 the duration interval, then the selected interval is a short A-A interval. Short A-A intervals are used to increment 1630 the odd sequence atrial tachyarrhythmia counter. Based on the atrial tachyarrhythmia counter, if the atrial tachyarrhythmia window is satisfied 1635 for odd sequence A-A intervals, e.g., if x out of y odd sequence A-A intervals are short A-A intervals, then atrial tachyarrhythmia is detected 1640. If the atrial tachyarrhythmia count is not satisfied, then A-A intervals are detected 1605.

If the A-A interval is 1610 an even numbered interval in the sequence, then the even numbered A-A interval is selected 1650 (FIG. 16B) to operate the even sequence atrial tachyarrhythmia counter.

The duration of the selected interval is compared to the duration of a detection interval. If the selected interval is longer than 1655 the duration interval, the selected A-A interval is a long A-A interval. Long A-A intervals are used to decrement 1660 the even sequence atrial tachyarrhythmia counter. If the selected A-A interval is shorter than 1655 the duration interval, then the selected interval is a short A-A interval. Short A-A intervals are used to increment 1665 the even sequence atrial tachyarrhythmia counter. If the atrial tachyarrhythmia window is satisfied 1635, e.g., if x out of y even sequence A-A intervals are short A-A intervals, then atrial tachyarrhythmia is detected 1640.

Figure 17:
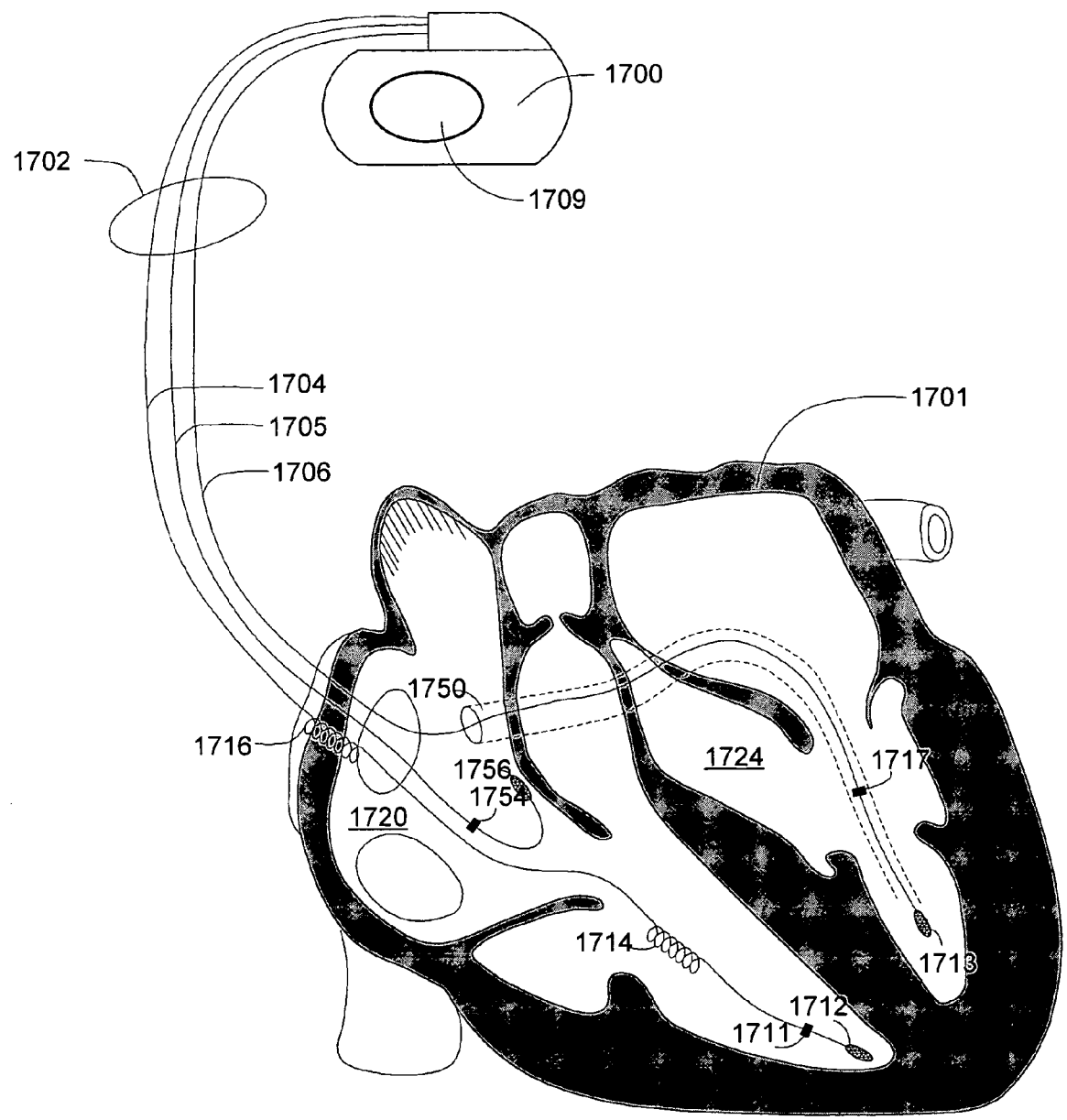
FIG. 17 is a partial view of a cardiac rhythm management (CRM) device that may be used to implement atrial tachyarrhythmia detection, classification and response in accordance with embodiments of the invention.

FIG. 17 is a partial view of a cardiac rhythm management (CRM) device that may be used to implement atrial tachyarrhythmia detection, classification and response in accordance with embodiments of the invention. Methods of the invention may be implemented in a variety of implantable or patient-external cardiac therapeutic and/or diagnostic devices including, for example, pacemakers, defibrillators, cardioverters, bi-ventricular pacemakers, and/or cardiac resynchronization devices, among others. The CRM device illustrated in FIG. 17 includes an implantable housing 1700 containing circuitry electrically coupled to an intracardiac lead system 1702. Portions of the implantable housing may be configured as a can electrode 1709. The housing 1700 and the intracardiac lead system 1702 is implanted in a human body with portions of the intracardiac lead system 1702 inserted into a heart 1701. The intracardiac lead system 1702 is used to detect electric cardiac signals produced by the heart 1701 and to provide electrical energy to the heart 1701 under predetermined conditions to treat cardiac arrhythmias.

The intracardiac lead system 1702 includes one or more electrodes used for pacing, sensing, and/or defibrillation. In the particular embodiment shown in FIG. 17, the intracardiac lead system 1702 includes a right ventricular lead system 1704, a right atrial lead system 1705, and a left ventricular lead system 1706. In one embodiment, the right ventricular lead system 1704 is configured as an integrated bipolar pace/shock lead.

The right ventricular lead system 1704 includes an SVC-coil 1716, an RV-coil 1714, and an RV-tip electrode 1712. The RV-coil 1714, which may alternatively be configured as a separate defibrillation coil and an RV-ring electrode 1711, is spaced apart from the RV-tip electrode 1712, which is a pacing electrode for the right ventricle.

The right atrial lead system 1705 includes a RA-tip electrode 1756 and an RA-ring electrode 1754. The RA-tip 1756 and RA-ring 1754 electrodes may provide pacing pulses to the right atrium of the heart and may also be used to detect cardiac signals from the right atrium. In one configuration, the right atrial lead system 1705 is configured as a J-lead.

In the configuration of FIG. 17, portions of the intracardiac lead system 1702 are shown positioned within the heart 1701, with the right ventricular lead system 1704 extending through the right atrium and into the right ventricle. Typical locations for placement of the RV-tip electrode 1712 are at the right ventricular (RV) apex or the RV outflow tract.

In particular, the RV-tip electrode 1712 and RV-coil electrode 1714 are positioned at appropriate locations within the right ventricle. The SVC-coil 1716 is positioned at an appropriate location within a major vein leading to the right atrium chamber of the heart 1701. The RV-coil 1714 and SVC-coil 1716 depicted in FIG. 17 are defibrillation electrodes.

The left ventricular lead system 1706 is advanced through the superior vena cava (SVC), the right atrium 1720, the ostium of the coronary sinus, and the coronary sinus 1750. The left ventricular lead system 1706 is guided through the coronary sinus 1750 to a coronary vein of the left ventricle 1724. This vein is used as an access pathway for leads to reach the surfaces of the left atrium and the left ventricle which are not directly accessible from the right side of the heart. Lead placement for the left ventricular lead system may be achieved via subclavian vein access and a preformed guiding catheter for insertion of the left ventricular (LV) electrodes 1713 and 1717 adjacent the left ventricle. In one configuration, the left ventricular lead system 1706 is implemented as a single-pass lead.

An LV distal electrode 1713, and an LV proximal electrode 1717 may be positioned adjacent to the left ventricle. The LV proximal electrode 1717 is spaced apart from the LV distal electrode, 1713 which is a pacing electrode for the left ventricle. The LV distal 1713 and LV proximal 1717 electrodes may also be used for sensing the left ventricle.

The lead configurations illustrated in FIG. 17 represent one illustrative example. Additional lead/electrode configurations may include additional and/or alternative intracardiac electrodes and/or epicardial electrodes. For example, in one configuration, an extracardiac lead may be used to position epicardial electrodes adjacent the left atrium for delivering electrical stimulation to the left atrium and/or sensing electrical activity of the left atrium.

Figure 18:
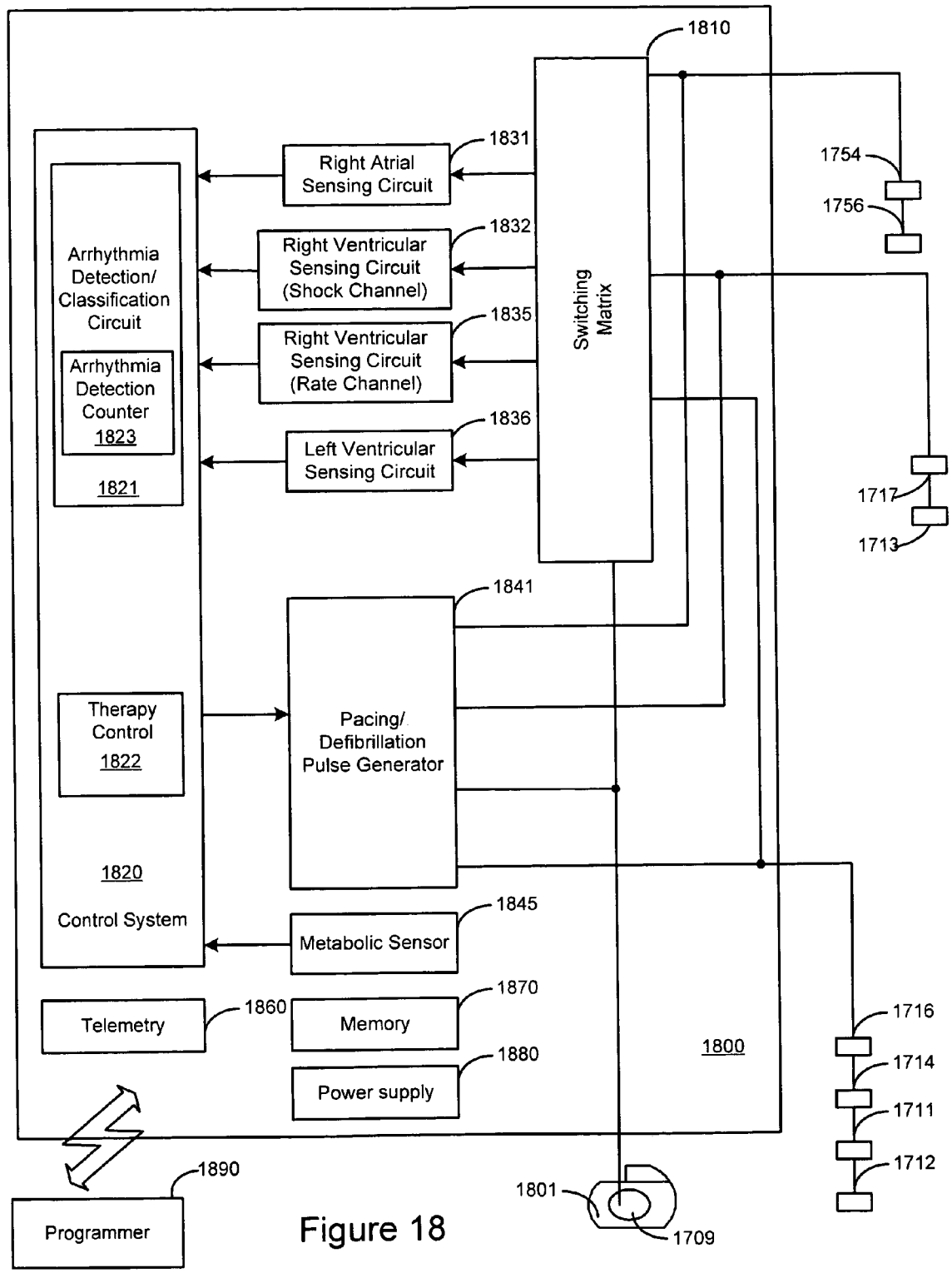
FIG. 18 is an illustration of a block diagram of a cardiac rhythm management (CRM) device suitable for implementing atrial tachyarrhythmia detection, classification, and response in accordance with embodiments of the invention.

Referring now to FIG. 18, there is shown a block diagram of a cardiac rhythm management (CRM) device 1800 suitable for implementing atrial tachyarrhythmia detection, classification, and response in accordance with embodiments of the invention. FIG. 18 shows a CRM device 1800 divided into functional blocks. It is understood by those skilled in the art that there exist many possible configurations in which these functional blocks can be arranged. The example depicted in FIG. 18 is one possible functional arrangement. Various functions of the CRM device 1800 may be accomplished by hardware, software, or a combination of hardware and software.

The CRM device 1800 includes components for sensing cardiac signals from a heart and delivering therapy, e.g., pacing pulses or cardioversion/defibrillation shocks, to the heart. The circuitry of the CRM device 1800 may be encased and hermetically sealed in a housing 1801 suitable for implanting in a human body. Power to the circuitry is supplied by an electrochemical battery power supply 1880 that is enclosed within the housing 1801. A connector block with lead terminals (not shown) is additionally attached to housing 1801 to allow for the physical and electrical attachment of the intracardiac lead system conductors to the encased circuitry of the CRM device 1800.

In one embodiment, the CRM device 1800 includes programmable microprocessor-based circuitry, including control circuitry 1820, a memory circuit 1870, sensing circuitry 1831, 1832, 1835, 1836, and a pulse generator 1841. Components of the CRM device 1800 cooperatively perform operations involving atrial tachyarrhythmia detection according to the approaches of the present invention. The control circuitry 1820 is responsible for arrhythmia detection, classification, and therapy control. The control circuitry 1820 may encompass various functional components, for example, an arrhythmia detection/classification circuit 1821, an arrhythmia counter 1823 and a therapy control unit 1822. The arrhythmia detection/classification circuit 1821 performs processes described above including selecting and using A-A intervals for atrial tachyarrhythmia detection and/or classification. The arrhythmia counter 1823 is used to count selected intervals for arrhythmia detection and/or classification. The arrhythmia detection/classification circuit 1821 may be used in connection with determining an appropriate response to atrial tachyarrhythmia, e.g., pace mode switching or therapy to treat the atrial tachyarrhythmia.

The memory circuit 1870 may store program instructions used to implement the functions of the CRM device 1800 as well as data acquired by the CRM device 300. For example, the memory circuit 1870 may store historical records of sensed cardiac signals, including arrhythmic episodes, and/or information about therapy delivered to the patient. The memory circuit 1870 may also store morphology templates representative of cardiac beats associated with various types of cardiac rhythms.

The historical data stored in the memory 1870 may be used for various purposes, including diagnosis of patient diseases or disorders. Analysis of the historical data may be used to adjust the operations of the CRM device 1800. Data stored in the memory 370 may be transmitted to an external programmer unit 1890 or other computing device, such as an advanced patient management system as needed or desired.

Telemetry circuitry 1860 allows the CRM device 1800 to communicate with an external programmer unit 1890 and/or other remote devices. In one embodiment, the telemetry circuitry 1860 and the external programmer unit 1890 use a wire loop antenna and a radio frequency telemetric link to receive and transmit signals. In this manner, programming commands and data may be transferred between the CRM device 1800 and the external programmer 1890 after implant.

The CRM device 1800 may function as a pacemaker and/or a defibrillator. As a pacemaker, the CRM device 1800 delivers a series of electrical stimulations to the heart to regulate heart rhythm. Therapy control circuitry 1822 controls the delivery of pacing pulses to treat various arrhythmic conditions of the heart, for example. In various embodiments, the CRM device 1800 may deliver pacing pulses to one or more of the right atrium, left atrium, right ventricle and the left ventricle. The heart may be paced to treat bradycardia, or to synchronize and/or coordinate contractions of the right and left ventricles.

For example, right ventricular pacing may be implemented using unipolar or bipolar configurations. Unipolar RV pacing involves, for example, pacing pulses delivered between the RV-tip 1712 to can 1709 electrodes. Bipolar pacing involves, for example, delivery of pacing pulses between the RV-tip 1712 to RV-coil 1714 electrodes. If an RV-ring electrode is present, bipolar pacing may be accomplished by delivering the pacing pulses to the RV-tip 1712 and RV-ring 1711 electrodes.

Left ventricular pacing may be implemented using unipolar or bipolar configurations. Unipolar LV pacing may include, for example, pacing pulses delivered between the LV distal electrode 1713 and the can 1709. Alternatively, bipolar LV pacing may be accomplished by delivering the pacing pulses using the LV distal electrode 1713 and the LV proximal electrode 1717.

Similarly, unipolar (RA-tip electrode 1756 to can electrode 1709) atrial pacing or bipolar (RA-tip electrode 1756 to RA-ring electrode 1754) atrial pacing may be provided by the CRM device 1800.

The CRM device 1800 may also provide tachyarrhythmia therapy. For example, tachyarrhythmia therapy may be provided in the form of anti-tachycardia pacing (ATP) pulses delivered to an atrium or a ventricle. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length. ATP therapy may be delivered to treat atrial flutter, for example. Therapy for atrial fibrillation may involve cardioversion shocks to the heart that may be initiated automatically or by the patient. Life threatening arrhythmias, such as ventricular fibrillation may be treated by one or more defibrillation shocks to the heart to terminate the fibrillation.

In the embodiment depicted in FIG. 18, electrodes RA-tip 1756, RA-ring 1754, RV-tip 1712, RV-ring 1711, RV-coil 1714, SVC coil 1716, LV distal electrode 1713, LV proximal electrode 1717, and can 1709 are coupled through a switching matrix 1810 to various sensing circuits 1831, 1832, 1835, 1836. A right atrial sensing channel circuit 1831 serves to sense and amplify electrical signals from the right atrium of the heart. For example, bipolar sensing in the right atrium may be implemented by sensing signals developed between the RA-tip 1756 and RA-ring 1754 electrodes. The switch matrix 1810 may be operated to couple the RA-tip 1756 and RA-ring 1754 electrodes to the RA sensing channel circuit 1831 to effect bipolar sensing of right atrial signals. Alternatively, unipolar right atrial sensing may be accomplished by operating the switch matrix 1810 to couple the RA-tip 1756 and can 1709 electrodes to the RA sensing channel circuit 1831.

Cardiac signals sensed through the use of the RV-tip electrode 1712 and RV-coil 1714 or RV-ring electrode 1711 are right ventricular (RV) near-field signals and are referred to as RV rate channel signals herein. Bipolar rate channel sensing may be accomplished by operating the switch matrix 1810 to couple the RV-tip electrode 1712 and the RV-coil 1714 electrode or the RV-ring electrode 1711 through the RV rate channel sensing circuitry 1835. The rate channel signal may be detected, for example, as a voltage developed between the RV-tip electrode 1712 and the RV-coil 1714 electrode or the RV-ring electrode 1711. The RV rate channel sensing circuitry 1835 serves to sense and amplify the RV rate channel signal.

Unipolar RV sensing may be implemented, for example, by coupling the RV-tip 1712 and can 1709 electrodes to the RV rate channel sensing circuitry 1835. In this configuration, the rate channel signal is detected as a voltage developed between the RV-tip 1712 to can 1709 sensing vector.

The RV lead system may also include an RV-ring electrode 1711 used for bipolar pacing and sensing. If an RV-ring electrode is included in the lead system, bipolar sensing may be accomplished by sensing a voltage developed between the RV-tip 1712 and RV-ring 1711 electrodes.

Far-field signals, such as cardiac signals sensed through use of one of the defibrillation coils or electrodes 1714, 1716 and the can 1709, or using both of the defibrillation coils or electrodes 1714, 1716, are referred to as morphology or shock channel signals herein. The shock channel signal may be detected as a voltage developed between the RV-coil 1714 to the can electrode 209, the RV-coil 1714 to the SVC-coil 1716, or the RV-coil 1714 to the can electrode 1709 shorted to the SVC-coil 1716. The switch matrix 1810 is operated to couple the desired shock channel sensing vector, e.g., RV-coil to can, to the right ventricular shock channel sensing circuitry 1832. The RV shock channel sensing circuitry 1832 serves to sense and amplify the shock channel signal.

The outputs of the switching matrix 1810 may also be operated to couple selected combinations of the electrodes to LV sensing channel circuitry 1836 for sensing electrical activity of the left ventricle. Bipolar left ventricular sensing may be accomplished by operating the switch matrix 1810 to couple the LV-distal 1713 and the LV proximal electrodes 1717 through the LV channel sensing circuitry 1836. In this configuration, the LV signal is detected as a voltage developed between the LV proximal and LV distal electrodes.

Unipolar LV sensing may be implemented, for example, by coupling the LV distal 1713 and can 1709 electrodes to the LV sensing circuitry 1736. In this configuration, the LV signal is detected as a voltage developed between the RV-tip 1712 to can 1709 sensing vector.

The CRM device 1800 may incorporate one or more metabolic sensors 1845 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased to correspond to the level of activity or rate of respiration.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for detecting atrial tachyarrhythmia, comprising:

detecting a plurality of A-A intervals;

selecting A-A intervals from the plurality of A-A intervals based at least in part on one or more events occurring between consecutively sensed atrial depolarizations of the A-A intervals; and using the selected A-A intervals to detect atrial tachyarrhythmia;

wherein selecting the A-A intervals comprises:

determining if a particular A-A interval is a qualified A-A interval, comprising:

determining that the particular A-A interval is a qualified A-A interval if a duration of the particular A-A interval falls outside a predetermined duration range; and determining that the particular A-A interval is a qualified A-A interval based on events occurring between consecutively sensed atrial depolarizations of the particular A-A interval if the duration of the particular A-A interval falls within the predetermined duration range; and wherein using the selected interval comprises using the qualified A-A interval to detect atrial tachyarrhythmia.

2. The method of claim 1, wherein the duration range is greater than an atrial tachyarrhythmia response interval and less than twice the atrial tachyarrhythmia response interval.

3. A method for detecting atrial tachyarrhythmia, comprising:

detecting a plurality of A-A intervals;

selecting A-A intervals from the plurality of A-A intervals based at least in part on one or more events occurring between consecutively sensed atrial depolarizations of the A-A intervals; and using the selected A-A intervals to detect atrial tachyarrhythmia;

wherein selecting the A-A intervals comprises selecting an A-A interval based on a timing of a blanking period relative to a point within the A-A interval.

4. The method of claim 3, wherein the timing of the blanking period relative to the point within the A-A interval comprises a midpoint of the A-A interval that falls within the blanking period occurring between the consecutively sensed atrial depolarizations of the A-A interval.

5. A method for detecting atrial tachyarrhythmia, comprising:

detecting a plurality of A-A intervals;

selecting A-A intervals from the plurality of A-A intervals based at least in part on one or more events occurring between consecutively sensed atrial depolarizations of the A-A intervals; and using the selected A-A intervals to detect atrial tachyarrhythmia;

wherein selecting the A-A intervals comprises selecting based on one more criterion of a criteria set, the criteria set comprising:

a first selection criterion related to a timing of a blanking period relative to a point within the A-A interval; and a second selection criterion specifying that the A-A interval is not interrupted by a ventricular event.

6. A method for detecting atrial tachyarrhythmia, comprising:
- detecting a plurality of A-A intervals;
- selecting A-A intervals from the plurality of A-A intervals based at least in part on one or more events occurring between consecutively sensed atrial depolarizations of the A-A intervals; and
- using the selected A-A intervals to detect atrial tachyarrhythmia;

wherein using the selected A-A intervals to detect the atrial tachyarrhythmia comprises:
- operating a counter using qualified A-A intervals; and
- detecting the atrial tachyarrhythmia if the counter reaches a predetermined value.

\* \* \* \* \*

UNITED STATES PATENT AND TRADEMARK OFFICE
CERTIFICATE OF CORRECTION

PATENT NO. : 7,580,740 B2  Page 1 of 1
APPLICATION NO. : 11/126594
DATED : August 25, 2009
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this

Fourteenth Day of September, 2010

David J. Kappos
*Director of the United States Patent and Trademark Office*